US009169492B2

(12) United States Patent                           (10) Patent No.:     US 9,169,492 B2
     Monahan et al.                                    (45) Date of Patent:      Oct. 27, 2015

(54) COMPOSITIONS AND METHODS FOR ENHANCED PARVOVIRUS TRANSDUCTION

(75) Inventors: Paul E. Monahan, Chapel Hill, NC (US); Richard Jude Samulski, Chapel Hill, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 0 days.

(21) Appl. No.: 13/575,975

(22) PCT Filed: Feb. 4, 2011

(86) PCT No.: PCT/US2011/023715
    § 371 (c)(1),
    (2), (4) Date: Oct. 1, 2012

(87) PCT Pub. No.: WO2011/097456
    PCT Pub. Date: Aug. 11, 2011

(65) Prior Publication Data
    US 2013/0012574 A1    Jan. 10, 2013

(51) Int. Cl.
    C12N 15/864    (2006.01)
    A61K 48/00     (2006.01)
    C12N 15/86     (2006.01)
    A61K 31/69     (2006.01)
    A61K 45/06     (2006.01)

(52) U.S. Cl.
    CPC ............... *C12N 15/86* (2013.01); *A61K 31/69* (2013.01); *A61K 45/06* (2013.01); *A61K 48/00* (2013.01); *C12N 2750/14143* (2013.01)

(58) Field of Classification Search
    None
    See application file for complete search history.

(56) References Cited

U.S. PATENT DOCUMENTS

| 6,924,365 | B1  | 8/2005  | Miller et al.                 |
| 7,241,447 | B1  | 7/2007  | Engelhardt et al.             |
| 7,749,491 | B2  | 7/2010  | Engelhardt et al.             |
| 7,803,622 | B2  | 9/2010  | Engelhardt et al.             |
| 2006/0093585 | A1* | 5/2006 | Engelhardt et al. ......... 424/93.2 |
| 2007/0042462 | A1* | 2/2007 | Hildinger ................ 435/69.1 |
| 2009/0004145 | A1  | 1/2009 | Ramesh                        |
| 2010/0255004 | A1* | 10/2010 | DePinho et al. ........... 424/172.1 |

FOREIGN PATENT DOCUMENTS

WO   WO 2007/149852 A2   12/2007
WO   WO 2008/088895 A2    7/2008

OTHER PUBLICATIONS

Grieger et al, Packaging Capacity of Adeno-Associated Virus Serotypes: Impact of Larger Genomes on Infectivity and Postentry Steps, Journal of Virology, Aug. 2005, p. 9933-9944.*

Nathwani et al, Enhancing Transduction of the Liver by Adenoassociated Viral Vectors, Gene Ther. Jan. 2009 ; 16(1): 60-69.*
Finn et al. "Proteasome Inhibitors Decrease AAV2 Capsid-Derived Peptide Epitope Presentation on MHC Class I Following Transduction" *Blood* 114(22):291 (2009).
Finn et al. "Proteasome Inhibitors Decrease AAV2 Capsid-derived Peptide Epitope Presentation on MHC Class I Following Transduction" *Molecular Therapy* 18(1):135-142 (2010).
Grieger et al. "Packaging Capacity of Adeno-Associated Virus Serotypes: Impact of Larger Genomes on Infectivity and Postentry Steps" *Journal of Virology* 79(15):9933-9944 (2005).
Nathwani et al. "Enhancing transduction of the liver by adeno-associated viral vectors" *Gene Therapy* 16:60-69 (2009).
Sun et al. "Proteasome Inhibitors Enhance Gene Delivery by Adeno-Associated Virus Vectors Carrying Large Genomes in Hemophilia Mouse and Dog Models" *Molecular Therapy* 17(1):S313-S314 (2009).
Adams et al. "Proteasome inhibitors: A novel class of potent and effective antitumor agents" *Cancer Research* 59:2615-2622 (1999).
Arastu-Kapur et al. "Nonproteasomal targets of the proteasome inhibitors bortezomib and carfilzomib: a link to clinical adverse events" *Clin Cancer Res* 17:2734-2743 (2011).
Blanco et al. "Bortezomib induces selective depletion of alloreactive T lymphocytes and decreases the production of Th1 cytokines" *Blood* 107:3575-3583 (2006).
Bowles et al. "Phase 1 gene therapy for duchenne muscular dystrophy using a translational optimized AAV vector" *Molecular Therapy* 20:443-455 (2012).
Chao et al. "Expression of human factor VIII by splicing between dimerized AAV vectors" *Mol Ther* 5:716-722 (2002).
Chen et al. "The enhancing effects of the light chain on heavy chain secretion in split delivery of factor VIII gene" *Mol Ther* 15:1856-1862 (2007).
Cheng et al. "Development of optimized AAV3 serotype vectors: Mechanism of high-efficiency transduction of human liver cancer cells" *Gene Ther*. 19(4):375-384 (2012).
Choi et al. "Production of recombinant adeno-associated viral vectors for in vitro and in vivo use" *Curr Protoc Mol Biol Chapter 16*:Unit 16 25 (2007).
Cockrell et al. "A trans-lentiviral packaging cell line for high-titer conditional self-inactivating HIV-1 vectors" *Mol Ther* 14:276-284 (2006).
Davidoff et al. "Sex significantly influences transduction of murine liver by recombinant adeno-associated viral vectors through an androgen-dependent pathway" *Blood* 102:480-488 (2003).
Demo et al. "Antitumor activity of PR-171, a novel irreversible inhibitor of the proteasome" *Cancer Res* 67(13):6383-6391 (2007).
Denby at al, "Adeno-associated virus (AAV)-7 and -8 poorly transduce vascular endothelial cells and are sensitive to proteasomal degradation" *Gene Therapy* 12:1534-1538 (2005).
Dong et al. "Quantitative analysis of the packaging capacity of recombinant adeno-associated virus" *Hum Gene Ther* 7:2101-2112 (1996).
Douar et al. "Intracellular trafficking of adeno-associated virus vectors: routing to the late endosomal compartment and proteasome degradation" *J Virol* 75:1824-1833 (2001).

(Continued)

*Primary Examiner* — Maria Marvich
(74) *Attorney, Agent, or Firm* — Myers Bigel Sibley & Sajovec, P.A.

(57)    ABSTRACT

The present invention provides methods and compositions for enhanced transduction of an adeno-associated virus (AAV) vector comprising a heterologous nucleic acid of interest wherein the AAV vector genome is oversized relative to a wild type AAV genome by employing a proteasome inhibitor.

13 Claims, 8 Drawing Sheets

(56) References Cited

OTHER PUBLICATIONS

Duan et al. "Endosomal processing limits gene transfer to polarized airway epithelia by adeno-associated virus" *J Clin Invest* 105:1573-1587 (2000).
Duan et al. "Expanding AAV packaging capacity with trans-splicing or overlapping vectors: A quantitative comparison" *Molecular Therapy* 4:383-391 (2001).
Elliott et al. "Proteasome inhibition: a new anti-inflammatory strategy" *J Mol Med* 81:235-245 (2003).
Everly et al. "Proteasome inhibition for antibody-mediated rejection" *Curr Opin Organ Transplant*:14(6):662-666 (2009)(abstract only).
Harousseau et al. "Bortezomib plus dexamethasone as induction treatment prior to autologous stem cell transplantation in patients with newly diagnosed multiple myeloma: results of an IFM phase II study" *Haematologica* 91:1498-1505 (2006).
Hermonat et al. "The packaging capacity of adeno-associated virus (AAV) and the potential for wild-type plus AAV gene therapy vectors" *FEBS Lett* 407:78-84 (1997).
Herzog et al. "Muscle-directed gene transfer and transient immune suppression result in sustained partial correction of canine hemophilia B caused by a null mutation" *Mol Ther* 4:192-200 (2001).
Hirsch et al. "Little vector, big gene transduction: fragmented genome reassembly of adeno-associated virus" *Molecular Therapy* 18:6-8 (2010).
Jagannath et al. "Bortezomib therapy alone and in combination with dexamethasone for previously untreated symptomatic multiple myeloma" *Br J Haematol* 129:776-783 (2005).
Jennings et al. "Proteasome inhibition enhances AAV-mediated transgene expression in human synoviocytes in vitro and in vivo" *Mol Ther* 11:600-607 (2005).
Jiang et al. "Multiyear therapeutic benefit of AAV serotypes 2, 6 and 8 delivering factor VIII to hemophilia A mice and dogs" *Blood* 108:107-115 (2006).
Jin et al. "Creation of a mouse expressing defective human factor IX" *Blood* 104:1733-1739 (2004).
Johnson et al. "Enhancement of adeno-associated virus infection by mobilizing capsids into and out of the nucleolus" *J Virol* 83:2632-2644 (2009).
Johnson et al. "Mutagenesis of adeno-associated virus type 2 capsid protein VP1 uncovers new roles for basic amino acids in trafficking and cell-specific transduction" *Journal of Virology* 84:8888-8902 (2010).
Kahn et al. "Immunoproteasomes largely replace constitutive proteasomes during an antiviral and antibacterial immune response in the liver" *J Immunol* 167:6859-6868 (2001).
Kuhn et al. "Potent activity of carfilzomib, a novel, irreversible inhibitor of the ubiquitin-proteasome pathway, against preclinical models of multiple myeloma" *Blood* 110:3281-3290 (2007).
Landowski at al. "Mitochondrias-mediated disregulation of $Ca^2+$ is a critical determinant of Velcade (PS-341/bortezomib) cytotoxicity in myeloma cell lines" *Cancer Res* 65:3828-3836 (2005).
LeBlanc et al. "Proteasome inhibitor PS-341 inhibits human myeloma cell growth in vivo and prolongs survival in a murine model" *Cancer Res* 62:4996-5000 (2002).
Mitchell et al "Mechanistic insights into the enhancement of adeno-associated virus transduction by proteasome inhibitors" *Journal of Virology* 87:13035-13041 (2013).
Monahan et al. "Proteasome inhibitors enhance gene delivery by AAV virus vectors expressing large genomes in hemophilia mouse and dog models: a strategy for broad clinical application" *Molecular Therapy* 18(11):1907-1916 (2010).
Mount et al. "Sustained phenotypic correction of hemophilia B dogs with a factor IX null mutation by liver-directed gene therapy" *Blood* 99:2670-2767 (2002).
Muchamuel et al. "A selective inhibitor of the immunoproteasome submit LMP7 blocks cytokine production and attenuates progression of experimental arthritis" *Nat Med* 15:781-787 (2009).

Pajusola et al. "Cell-type specific characteristics modulate the transduction efficiency of adeno-associated virus type 2 and restrain infection of endothelial cells" *Journal of Virology* 76:11530-11540 (2002).
Ponder "Gene therapy for hemophilia" *Curr Opin Hematol* 13:301-307 (2006).
Rotundo et al. "Use of a lower dosage liver-detargeted AAV vector to prevent hamster muscular dystrophy" *Human Gene Therapy* 24:1-7 (2013).
Sarker et al. "Total correction of hemophilia A mice with canine FVIII using an AAV 8 serotype" *Blood* 103:1253-1260 (2006).
Sarkar et al. "Long-term efficacy of adeno-associated virus serotypes 8 and 9 in hemophilia A dogs and mice" *Hum Gene Ther* 17:427-439 (2006).
Sasgary et al. "Single cell analysis of factor VIII-specific T cells in hemophilic mice after treatment with human factor VIII" *Thromb Haemost* 87:266-272 (2002).
Scallan et al. "Sustained phenotypic correction of canine hemophilia A using an adeno-associated viral vector" *Blood* 102:2031-2037 (2003).
Sood et al. "Retreatment with bortezomib alone or in combination for patients with multiple myeloma following an initial response to bortezomib" *Am J Hematol* 84:657-660 (2009).
Thomas et al. "Rapid uncoating of vector genomes is the key to efficient liver transduction with pseudotyped adeno-associated virus vectors" *J Virol* 78:3110-3122 (2004).
Waters et al. "Anti-CD3 prevents factor VIII inhibitor development in hemophilia A mice by a regulatory CD4+CD25+-dependent mechanism and by shifting cytokine production to favor a Th1 response" *Blood* 113:193-203 (2009)(abstract only).
Wang et al. "Adeno-associated virus vector carrying human minidystrophin genes effectively ameliorates muscular dystrophy in mdx mouse model" *Proc Natl Acad Sci USA* 97:13714-13719 (2000).
Wu et al. "Optimization of self-complementary AAV vectors for liver-directed expression results in sustained correction of hemophilia B at low vector dose" *Mol Ther* 16:280-289 (2008).
Wu et al. "Mechanism of the immune response to human factor VIII in murine hemophilia A" *Thromb Haemost* 85:125-133 (2001)(abstract only).
Yan et al. "Ubiquitination of both adeno-associated virus type 2 and 5 capsid proteins affects the transduction efficiency of recombinant vectors" *J Virol* 76:2043-2053 (2002).
Yan et al. "Distinct classes of proteasome-modulating agents cooperatively augment recombinant adeno-associated virus type 2 and type 5-mediated transduction from the apical surfaces of human airway epithelia" *Journal of Virology* 78:2863-2874 (2004).
Zhang et al. "Efficient expression of CFTR function with adeno-associated virus vectors that carry shortened CFTR genes" *Proc Natl Acad Sci USA* 95:10158-10163 (1998).
Zhang et al. "Transgene expression levels and kinetics determine risk of humoral immune response modeled in factor IX knockout and missense mutant mice" *Gene Ther* 14:429-440 (2007).
Zhong et al. "Tyrosine-phosphorylation of AAV2 vectors and its consequences on viral intracellular trafficking and transgene expression" *Virology* 381(2):194-202 (2008).
Zhong et al. "Next generation of adeno-associated virus 2 vectors: Point mutations in tyrosines lead to high-efficiency transduction at lower doses" *Pro Natl Acad Sci USA* 105:7827-7832 (2008).
Zhu et al. "Sustained whole-body functional rescue in congestive heart failure and muscular dystrophy hamsters by systemic gene transfer" *Circulation* 112:2650-2659 (2005).
Allocca et al. "Serotype-Dependent Packaging of Large Genes in Adeno-Associated Viral Vectors Results in Effective Gene Delivery in Mice" *The Journal of Clinical Investigation* 118(5):1955-1964 (2008).
Athanasopoulos et al. "Recombinant Adeno-Associated Viral (rAAV) Vectors as Therapeutic Tools for Duchenne Muscular Dystrophy (DMD)" *Gene Therapy* 11:S109-S121 (2004).
Dong et al. "Characterization of Genome Integrity for Oversized Recombinant AAV Vector" *Molecular Therapy* 18(1):87-92 (2010).

(56) References Cited

OTHER PUBLICATIONS

Lu et al. "Complete Correction of Hemophilia A with Adeno-Associated Viral Vectors Containing a Full-Size Expression Cassette" *Human Gene Therapy* 19(6):648-654 (2008) Abstract.

Neukirchen et al. "The Proteasome Inhibitor Bortezomib Acts Differently in Combination with p53 Gene Transfer or Cytotoxic Chemotherapy on NSCLC Cells" *Cancer Gene Therapy* 14:431-439 (2007).

PCT International Search Report and Written Opinion for International Application No. PCT/US2011/023715, mailed Oct. 17, 2011 (11 pages).

\* cited by examiner

COMPOSITIONS AND METHODS FOR ENHANCED PARVOVIRUS TRANSDUCTION

STATEMENT OF GOVERNMENT SUPPORT

This invention was made with government support under Grant No. HL066973 awarded by the National Institutes of Health. The U.S. Government has certain rights in the invention.

STATEMENT OF PRIORITY

This application is a 35 U.S.C. §371 national phase application of International Application Serial No. PCT/US2011/023715, filed Feb. 4, 2011, which claims the benefit, under 35 U.S.C. §119(e), of U.S. Provisional Patent Application No. 61/301,998, filed Feb. 5, 2010, the disclosures of each of which are incorporated herein by reference in their entireties.

BACKGROUND OF THE INVENTION

It is known that parvoviruses, such as adeno-associated viruses (AAV), disfavor genomes that differ substantially in size from the wild-type genome (e.g., less than about 80 to 85% and greater than about 105 to 107% of wild-type size). This observation also holds true for recombinant parvovirus vectors, where it can limit the size of the transgene and/or regulatory sequences (such as promoters) that can be packaged and efficiently delivered by the vector to target cells.

The present invention overcomes previous shortcomings in the art by providing adenovirus vectors that contain an oversized AAV genome comprising a heterologous nucleotide sequence, and methods of their use

SUMMARY OF THE INVENTION

In one aspect, the present invention provides a composition comprising: (a) an adeno-associated virus (AAV) vector comprising a heterologous nucleic acid of interest wherein the AAV vector genome is oversized relative to a wild type AAV genome; and (b) a proteasome inhibitor. In some embodiments, the size of the AAV vector genome can be greater than about 5.2 kb and in further embodiments, the AAV vector can comprise single stranded AAV vector genome, a double-stranded MV vector genome or a self-complementary AAV vector genome.

In various embodiments of this invention, the proteasome inhibitor can be bortezomib (Velcade®).

In various embodiments of this invention, the heterologous nucleic acid of interest can encode a clotting factor, which can be Factor VIII (FVIII). In some embodiments the heterologous nucleic acid of interest can encode dystrophin.

In some embodiments of this invention, the heterologous nucleic acid can comprise a coding sequence that has been optimized relative to a wild type nucleotide sequence. In other embodiments, the heterologous nucleic acid can comprise noncoding sequences that have been optimized relative to wild type noncoding sequences. In yet further embodiments, the AAV vector genome can be optimized relative to a wild type AAV genome.

Further aspects of this invention include a pharmaceutical formulation comprising a composition of this invention in a pharmaceutically acceptable carrier.

The present invention further provides various methods, including a method of delivering a nucleic acid of interest to a cell, comprising introducing the composition or the pharmaceutical formulation of this invention into the cell.

Also provided herein is a method of delivering a nucleic acid of interest to a subject (e.g., a subject in need thereof), comprising administering the composition or the pharmaceutical formulation of this invention to the subject.

Additional aspects of this invention include a method of delivering a nucleic acid of interest to a cell, comprising contacting the cell with: (a) an adeno-associated virus (AAV) vector comprising a heterologous nucleic acid of interest wherein the AAV vector genome is oversized as compared to a wild type AAV genome; and (b) a proteasome inhibitor.

Also provided herein is a method of delivering a nucleic acid of interest to a subject (e.g., a subject in need thereof), comprising administering to the subject: (a an adeno-associated virus (AAV) vector comprising a heterologous nucleic acid of interest wherein the AAV vector genome is oversized as compared to a wild type AAV genome; and (b) a proteasome inhibitor.

In methods involving a cell, the cell can be a muscle cell and/or a liver cell and/or a cell in a joint or osteochondral site.

Furthermore, in the methods of this invention, the AAV vector can be administered before, after and/or concurrently with the administration of the proteasome inhibitor, in any combination.

In the methods of this invention, the proteasome inhibitor can be bortezomib (Velcade®). Also in the methods of this invention, the heterologous nucleic acid of interest can encode FVIII. In other embodiments, the heterologous nucleic acid of interest can encode dystrophin.

Additionally, in the methods of this invention, the heterologous nucleic acid or nucleotide sequence can comprise a coding sequence that has been optimized relative to a wild type nucleotide sequence. In other embodiments, the heterologous nucleic acid or nucleotide sequence can comprise noncoding sequences that have been optimized relative to wild type noncoding sequences. In yet further embodiments, the AAV vector genome can be optimized relative to a wild type AAV genome.

Yet further aspects of this invention include a kit comprising: (a) an adeno-associated virus (AAV) vector comprising a heterologous nucleic acid of interest wherein the AAV vector genome is oversized as compared to a wild type AAV genome; and (b) a proteasome inhibitor. The kit of this invention can comprise a heterologous nucleic acid of interest that encodes FVIII. A kit of this invention can also comprise a heterologous nucleic acid of interest that encodes dystrophin.

In the kit of this invention, the proteasome inhibitor can be bortezomib (Velcade®).

The present invention further provides a method of treating hemophilia A in a subject (e.g., a human subject), comprising administering to the subject: (a) an AAV vector comprising a heterologous nucleotide sequence encoding FVIII; and (b) bortezomib (Velcade®).

As note above, in such methods of treatment the heterologous nucleic acid or nucleotide sequence encoding FVIII can comprise a coding sequence that has been optimized relative to a wild type nucleotide sequence. In other embodiments, the heterologous nucleic acid or nucleotide sequence encoding FVIII can comprise noncoding sequences that have been optimized relative to wild type noncoding sequences. In yet further embodiments, the AAV vector genome can be optimized relative to a wild type AAV genome.

In the methods of treating hemophilia A, the MV vector can be administered before, after and/or concurrently with the administration of the bortezomib (Velcade®), in any combination. In particular embodiments, the AAV vector is administered before the administration of the bortezomib (Velcade®).

Further provided herein is a method of treating muscular dystrophy in a subject (e.g., a human subject), comprising administering to the subject: (a) an AAV vector comprising a heterologous nucleotide sequence encoding dystrophin; and (b) bortezomib (Velcade®).

Additionally, in the treatment methods of this invention, the heterologous nucleic acid or nucleotide sequence encoding dystrophin can comprise a coding sequence that has been optimized relative to a wild type nucleotide sequence. In other embodiments, the heterologous nucleic acid or nucleotide sequence encoding dystrophin can comprise noncoding sequences that have been optimized relative to wild type noncoding sequences. In yet further embodiments, the AAV vector genome can be optimized relative to a wild type AAV genome.

In the methods of treating muscular dystrophy, the AAV vector can be administered before, after and/or concurrently with the administration of the bortezomib (Velcade®), in any combination. In particular embodiments, the AAV vector is administered before the administration of the bortezomib (Velcade®).

In particular embodiments of the compositions and methods of this invention, the AAV vector is AAV type 8. In some embodiments of this invention, the AAV vector is AAV type 2. In some embodiments of this invention, the AAV vector is AAV type 5.

Particular embodiments of this invention are directed to parvovirus vectors for the delivery of nucleic acids to cells, both in vitro and in vivo, in combination or temporal association with administration of Velcade® or alternative compounds with similar mechanisms of action. Additional embodiments are directed to delivery of novel modified blood coagulation factors e.g., delivery of AAV encoding codon optimized Coagulation Factor VIII (e.g., as described in PCT/US2007/071553, the disclosure of which is incorporated herein by reference in its entirety) in combination or temporal association with Velcade®.

DETAILED DESCRIPTION OF THE INVENTION

Figure 1:
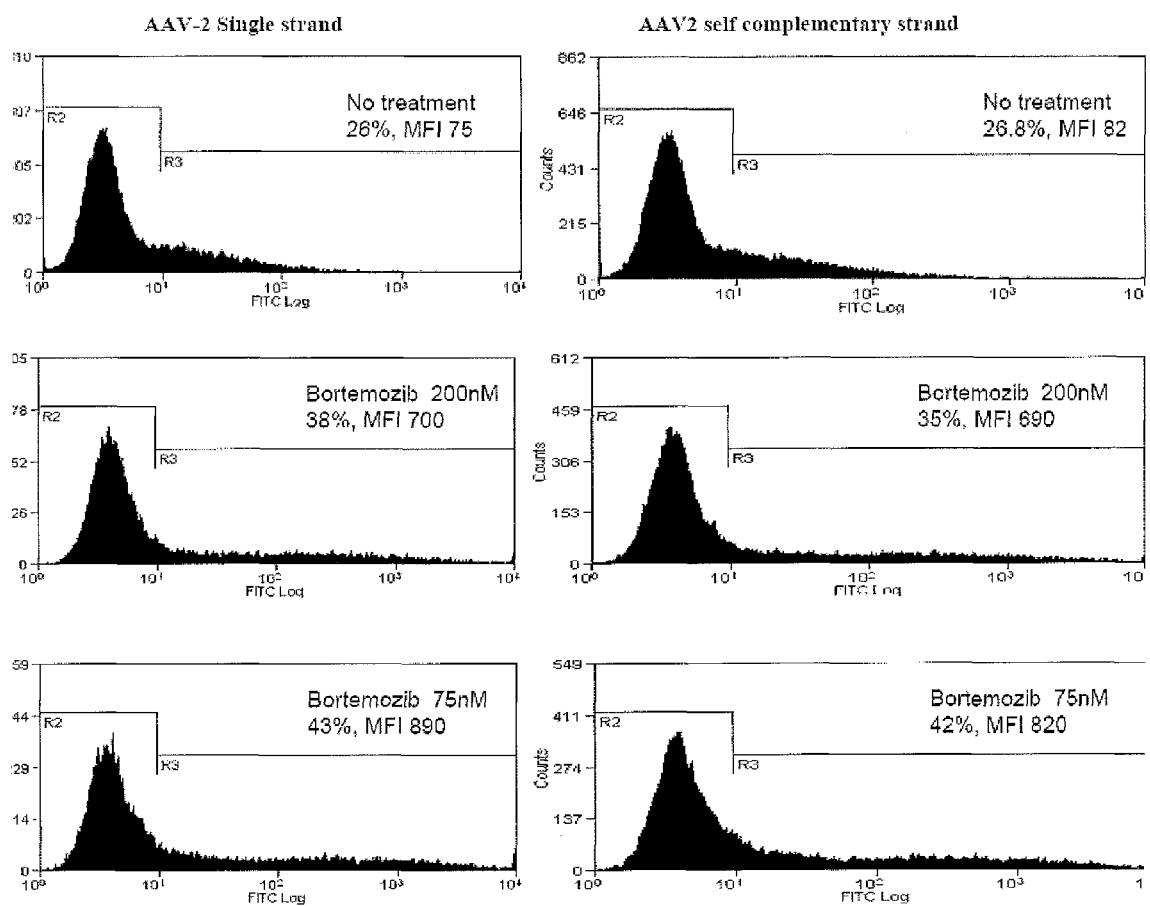
FIG. 1. Proteasome inhibitor increases expression of AAV-2 vectors in vitro. Fluorescence-activated cell sorting analysis of green fluorescent protein (GFP) expression in 293T cells transduced with conventional single strand AAV2 (left panels) and with self-complementary AAV2 vectors (right panel) in the presence or absence of the proteasome inhibitor, bortezomib. Mean fluorescence intensity (MFI) and percentage of GFP positive cells are indicated. Untransduced 293T cells served as a negative control.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. §1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

DEFINITIONS

As used herein, "a," "an" and "the" can mean one or more than one, depending on the context in which it is used. For example, "a" cell can mean one cell or multiple cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in activity of at least about 50% or more as compared to the activity of a polypeptide consisting of the recited sequence.

The term "parvovirus" as used herein encompasses the family Parvoviridae, including autonomously replicating parvoviruses and dependoviruses. The autonomous parvoviruses include members of the genera *Parvovirus, Eythrovirus, Densovirus, Iteravirus*, and *Contravirus*. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, ovine AAV, and any other AAV now known or later discovered. See, e.g., BERNARD N, FIELDS et al., VIROLOGY, volume 2, chapter 69 (4th ed., Lippincott-Raven Publishers). Recently, a number of putative new AAV serotypes and clades have been identified (see, e.g., Gao et al., (2004) *J. Virology* 78:6381-6388; Moris et al., (2004) *Virology* 33:375-383; and Table 5).

The genomic sequences of the various serotypes of AAV and the autonomous parvoviruses, as well as the sequences of the terminal repeats (TRs), Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, 089790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al., (1983) *J. Virology* 45:555; Chiorini et al., (1998) *J. Virology* 71:6823; Chiorini et al., (1999) *J. Virology* 73:1309; Bantel-Schaal et al., (1999) *J. Virology* 73:939; Xiao et al., (1999) *J. Virology* 73:3994; Muramatsu et al., (1996) *Virology* 221:208; Shade et al., (1986) *J. Virol.* 58:921; Gao et al., (2002) *Proc. Nat. Acad. Sci. USA* 99:11854; Moris et al., (2004) *Virology* 33:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences.

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form in which the virus may take within the cell.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide.

As used herein, by "isolate" or "purify" (or grammatical equivalents) a virus vector, it is meant that the virus vector is at least partially separated from at least some of the other components in the starting material.

A "therapeutic polypeptide" is a polypeptide that can alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

By the terms "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder. Thus, the terms "treat," "treating" or "treatment of" (or grammatically equivalent terms) refer to both prophylactic and therapeutic regimens.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment of disease, in particular cancer or tumors (e.g., by causing regression of a cancer or tumor and/or by preventing metastasis and/or by preventing growth of metastatic nodules). The protective effects may be complete or partial, as long as the benefits of the treatment outweigh any disadvantages thereof.

According to the foregoing methods of inducing an immune response in a subject, the virus vector comprising the heterologous nucleotide sequence can be administered in an immunogenically effective amount, as described below.

A "heterologous nucleotide sequence" or "heterologous nucleic acid" is a sequence that is not naturally occurring in the virus. Generally, the heterologous nucleic acid comprises an open reading frame that encodes a polypeptide or non-translated RNA of interest (e.g., for delivery to a cell or subject). The heterologous nucleotide sequence or heterologous nucleic acid can also be a nucleotide sequence or nucleic acid that is not naturally occurring in a cell into which it is introduced or the heterologous nucleotide sequence or heterologous nucleic acid can be a nucleotide sequence or nucleic acid molecule that is the same as a nucleotide sequence or nucleic acid molecule that is naturally occurring but the heterologous nucleotide sequence or nucleic acid molecule is not present in the location or position where its naturally occurring counterpart is typically found and/or it is under the control of regulatory elements that that differ form those that regulate expression of the naturally occurring counterpart.

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within an AAV capsid. Alternatively, in some contexts, the term "vector" may be used to refer to the vector genome/vDNA alone.

A "rAAV vector genome" or "rAAV genome" is an AAV genome (i.e., vDNA) that comprises one or more heterologous nucleotide sequences. rAAV vectors generally require only the 145 base terminal repeat(s) (TR(s)) in cis to generate virus. All other viral sequences are dispensable and may be supplied in trans (Muzyczka, (1992) *Curr. Topics Microbiol. Immunol.* 158:97). Typically, the rAAV vector genome will only retain the minimal TR sequence(s) so as to maximize the size of the transgene that can be efficiently packaged by the vector. The structural and non-structural protein coding sequences may be provided in trans (e.g., from a vector, such as a plasmid, or by stably integrating the sequences into a packaging cell). The rAAV vector genome comprises at least one TR sequence (e.g., AAV TR sequence), optionally two TRs (e.g., two AAV TRs), which typically will be at the 5' and 3' ends of the heterologous nucleotide sequence(s), but need not be contiguous thereto. The TRs can be the same or different from each other.

An "AAV terminal repeat" or "AAV TR" may be from any AAV, including but not limited to serotypes 1, 2, 3, 4, 5, 6, 7, 8, 9, 10 or 11 or any other AAV now known or later discovered. The AAV terminal repeats need not have a wild-type terminal repeat sequence (e.g., a wild-type sequence may be altered by insertion, deletion, truncation or missense mutations), as long as the terminal repeat mediates the desired functions, e.g., replication, virus packaging, integration, and/or provirus rescue, and the like.

The term "terminal repeat" or "TR" includes any viral terminal repeat and synthetic sequences that form hairpin structures and function as an inverted terminal repeat, such as the "double-D sequence" as described in U.S. Pat. No. 5,478,745 to Samulski et al.

The capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al., (2002) *Proc. Nat. Acad. Sci.* 99:10405-10), AAV4 (Padron et al., (2005) *J. Virol.* 79: 5047-58), AAV5 (Walters et al., (2004) *J. Virol.* 78: 3361-71) and CPV (Xie et al., (1996) *J. Mol. Biol.* 6:497-520 and Tsao et al., (1991) *Science* 251: 1456-64).

The virus vectors of the invention can further be "targeted" virus vectors (e.g., having a directed tropism) and/or a "hybrid" parvovirus (i.e., in which the rAAV genome and viral capsid are from different parvoviruses) as described in international patent publication WO 00/28004 and Chao et al., (2000) *Molecular Therapy* 2:619 (the disclosures of which are incorporated herein by reference in their entireties).

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of this invention.

Further, the viral capsid or genome can contain other modifications, including insertions, deletions and/or substitutions.

Accordingly, as used herein, the term "virus vector" encompasses hybrid, targeted and duplexed virus particles, as well as other modified forms of parvoviruses and AAV.

The term "regulate," "regulates," or "regulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

As used herein, "transduction" refers to entry of a virus into the cell and expression (e.g., transcription and/or translation) of sequences delivered by the genome. In the case of a recombinant vector, "transduction" generally refers to entry of the recombinant virus into the cell and expression of a nucleic acid of interest delivered by the vector genome.

Also as used herein, "transgene" refers to any nucleic acid sequence used in the transfection or transduction (I.a, transformation) of a cell, which can be an in vitro cell or a cell in an organism. Thus, a transgene can be a coding sequence, a non-coding sequence, a cDNA, a gene or fragment or portion thereof, a genomic sequence, a regulatory element and the like. A "transgenic" organism, such as a transgenic plant or transgenic animal, is an organism into which a transgene has been delivered or introduced and the transgene can be expressed in the transgenic organism to produce a product, the presence of which can impart an effect (e.g., a therapeutic or beneficial effect) and/or a phenotype (e.g., a desired or altered phenotype) in the organism.

Furthermore, as used herein, an MV vector genome that is "oversized" relative to a wild type MV genome is an AAV genome that is greater than 4680 nucleotides (4.68 kb), which is the size of the wild type AAV genome. Such an oversized AAV vector genome can be, for example, 4.7 kb, 4.8 kb, 4.9 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, or 6.3 kb, etc.

"Enhanced" or "increased" transduction (and like terms) refers to any increase in transduction that is useful, e.g., for laboratory and/or clinical purposes. In particular embodiments, the compositions and methods of the present invention enhance or increase transduction of parvovirus vectors by at least about 10%, 15%, 20% 25%, 30%, 40%, 50%, 60% 75%, 90%, 100%, 150%, 200%, 250%, 300%, etc, as well as by at least about 2-fold, 3-fold, 5-fold, 10-fold, 15-fold, 25-fold, 50-fold, 75-fold, 100-fold, 500-fold, 1000-fold, 2000-fold, 5000-fold or more. The enhancement of or increase in transduction of the parvoviruses of this invention can be relative to a control or standard as would be well known in the art and as described herein.

"Enhanced" or "increased" expression (and like terms) refers to any increase in expression of a heterologous nucleic acid molecule of this invention that is useful, e.g., for laboratory and/or clinical purposes. In particular embodiments, the compositions and methods of the present invention enhance or increase expression of heterologous nucleic acid present in parvovirus vectors of this invention by at least about 10%, 15%, 20% 25%, 30%, 40%, 50%, 60% 75%, 90%, 100%, 150%, 200%, 250%, 300%, etc, as well as by at least about 2-fold, 3-fold, 5-fold, 10-fold, 15-fold, 25-fold, 50-fold, 75-fold, 100-fold, 500-fold, 1000-fold, 2000-fold, 5000-fold or more. The enhancement or increase in expression of a heterologous nucleic acid molecule of this invention can be relative to a control or standard as would be well known in the art and as described herein.

A "therapeutically effective" amount as used herein is an amount that is sufficient to provide some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

In some embodiments, cells that have been transduced with a virus vector may be administered to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response in the subject to which the pharmaceutical formulation is administered. In particular embodiments, the dosage is sufficient to produce a protective immune response (as defined herein). The degree of protection conferred need not be complete or permanent, as long as the benefits of administering the immunogenic polypeptide outweigh any disadvantages thereof.

The present invention is based, in part, on the discovery that recombinant parvovirus vector genomes that differ substantially from the wild-type in size can be packaged into virions and infect target cells; however, transduction by these virions is reduced at points post-entry into the target cell. Without being bound by any particular theory of the invention, it is believed that transduction by such vectors is inhibited at least in part by intracellular trafficking mechanisms and/or second-strand synthesis.

The inventors have found that proteasome inhibitors can enhance transduction by parvovirus vectors, including those delivering vector genomes that substantially differ in size from the wild-type genome. See, for example, Hirsch et al. "Little vector, big gene transduction: fragmented genome reassembly of adeno-associated virus" *Molecular Therapy* 18(1):6-8 (2010); Johnson & Samulski "Enhancement of adeno-associated virus infection by mobilizing capsids into and out of the nucleolus" *J. Virol.* 83(6):2632-2644 (2009); and Grieger and Samulski "Packaging capacity of adeno-associated virus serotypes: impact of larger genomes on infectivity and postentry steps" *J. Virol.* 79(15):9933-9944 (2005), the entire contents of each of which are incorporated by reference herein in their entireties.

Accordingly, as one aspect, the invention provides a composition comprising: (a) a parvovirus vector comprising a heterologous nucleic acid of interest; and (b) a proteasome inhibitor. In particular embodiments, the parvovirus vector is a hybrid AAV/autonomous parvovirus vector, e.g., comprising an AAV vector genome and an autonomous parvovirus capsid or vice versa. The parvovirus vector can further be a chimeric or targeted parvovirus vector (see, e.g., WO 00/28004 and Chao et al., (2000) *Molecular Therapy* 2:619.

In particular embodiments, the parvovirus comprises a genome that does not differ substantially in size from the size of the wild-type genome. In other embodiments, the size of the genome differs substantially from the wild-type size (e.g., less than about 80 to 85% and greater than about 105 to 107% of wild-type size).

In other representative embodiments, the parvovirus (e.g., an AAV) comprises an AAV vector genome that is greater than about 5.0, 5.2, 5.3, 5.4, or 5.5 kb and/or less than about 6, 6.1, 6.2, 6.3, 6.4 or 6.5 kb in size. In particular embodiments, the AAV vector genome is greater than about 5.2 kb and less than about 6.1 kb. In still further embodiments, the parvovirus (e.g., an AAV) comprises an AAV vector genome that is less than about 4.0, 3.9, 3.8, 3.7 or 3.6 kb in size.

According to the present invention, the parvovirus vector can comprise a single-stranded vector genome. Alternatively, the parvovirus vector can comprise a double-stranded vector genome. Double-stranded AAV vectors have been described, see, e.g., International Patent Publication No. WO 01/92551.

The present invention also encompasses a split transgene AAV vector, as is known in the art. (See, e.g., Chao et al. "Expression of human factor VIII by splicing between dimerized MV vectors" *Mol Ther* 5(6):716-722 (2002); Sarkar et al. "Total correction of hemophilia A mice with canine FVIII using an AAV8 serotype" *Blood* 103(4):1253-60 (2003); Chen et al. "The enhancing effects of the light chain on heavy chain secretion in split delivery of factor VIII gene" *Mol Ther* 15(10):1856-62 (2007); Lostal et al. "Efficient recovery of dysferlin deficiency by dual adeno-associated vector-mediated gene transfer" *Hum Mol Genet* 19(10):1897-1907 (2010); Halbert et al. "Efficient mouse airway transduction following recombination between AAV vectors carrying parts of a larger gene" *Nat Biotechnol* 20(7):697-701 (2002)).

The proteasome inhibitor can be any proteasome inhibitor now known or later discovered, including peptide analog and small molecule inhibitors. Numerous proteasome inhibitors are known in the art, and some have been used in cancer therapy. In particular embodiments, the proteasome inhibitor inhibits proteasomes that (1) cleave after hydrophobic side chains (chymotrypsin-like), (2) cleave after acidic side chains (postglutamyl peptidase), (3) cleave after basic side chains (trypsin-like), (4) cleave after branched-chain amino acids (BrAAP activity) or (5) cleave after small neutral amino acids (SNAAP activity).

In representative embodiments, the proteasome inhibitor is (1) a C-terminal peptide aldehyde, (2) a peptide vinyl sulfone (e.g., a peptide modified at the C-terminus by a vinyl sulfone moiety), (3) lactacysin, (4) a di- or tri-peptide aldehyde, (5) a peptide boron ester, (6) a peptide α-keto-carbonyl, (7) an α, β-epoxyketone, or (8) an anthracycline derivative.

In other particular embodiments, the proteasome inhibitor includes one or more of the following: N-acetyl-L-leucyl-L-leucyl-L-norleucine (LLnL), MG-132, PS-341 (bortezomib or Velcade™), doxorubicin, aclarubicin, aclacinomycin A, AdaAhx$_3$L$_3$VS, AdaLys(Bio)Ahx$_3$L$_3$VS, ALLM, ALLN, epoxomicin, α-methylomuralide, MG-115, NLVS, NP-LLL-VS, proteasome inhibitor I, proteasome inhibitor II, proteasome inhibitor III, proteasome inhibitor IV, proteasome inhibitor VII, tyropeptin A or YU101. Numerous proteasome inhibitors are available from commercial sources such as Calbiochem and Millenium Pharmaceuticals, Inc.

In some embodiments, the proteasome inhibitor of this invention can be administered with dexamethasone and in some embodiments, the proteasome inhibitor can be administered in the absence of administration of dexamethasone.

Proteasome inhibitors are known in the art and are described, for example, in Bogyo et al. (1997) *Biopoly* 43:269-280).

The parvovirus vector can comprise any heterologous nucleic acid sequence(s) of interest. Nucleic acid sequences of interest include nucleic acid sequences encoding polypeptides, including therapeutic (e.g., for medical or veterinary uses) or immunogenic (e.g., for vaccines) polypeptides.

As used herein, a heterologous nucleic acid or nucleotide sequence comprising a coding sequence that has been optimized relative to a wild type coding sequence (e.g., a coding sequence for FVIII or dystrophin) describes a coding sequence that has been optimized according to protocols well known in the art to, e.g., minimize usage of rare codons (e.g., human codons), remove alternative reading frames, etc., as would be known in the art (e.g., as described in PCT/US2007/071553, the disclosure of which is incorporated herein by reference in its entirety).

Also as used herein, a heterologous nucleic acid or nucleotide sequence comprising noncoding sequences that have been optimized relative to wild type noncoding sequences describes a heterologous nucleic acid or nucleotide sequence comprising noncoding sequences that have been optimized according to protocols well known in the art, e.g., to enhance the activity of the promoter, the poly A signal, terminal repeats and/or other noncoding elements, as well as to modulate the activity and/or function of cis elements and trans elements involved in gene expression, regulation and/or production, etc., as would be well known in the art.

Furthermore, as used herein, an AAV vector genome that has been optimized relative to a wild type AAV vector genome describes an MV vector in which the genome has been optimized to enhance the activity of viral cis elements required for replication, packaging and/or delivery, etc., as would be well known in the art. Such an optimized AAV vector can comprise an optimized transcription cassette, optimized terminal repeats, etc., as would be well known in the art.

Therapeutic polypeptides include, but are not limited to, cystic fibrosis transmembrane regulator protein (CFTR), dystrophin (including the protein product of dystrophin minigenes, see, e.g., Vincent et al., (1993) *Nature Genetics* 5:130; U.S. Patent Publication No. 2003/017131, utrophin (Tinsley et al., (1996) *Nature* 384:349), clotting factors and clotting factor regulatory proteins (e.g., Factor VIII, Factor IX, Factor X, von Willebrand factor, ADAMTS 13, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, α$_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor −3 and −4, brain-derived neurotrophic factor, bone morphogenic proteins [including RANKL and VEGF], glial derived growth factor, transforming growth factor −α and −β, and the like), lysosomal acid α-glucosidase, α-galactosidase A, receptors (e.g., the tumor necrosis growth factor α soluble receptor), anti-inflammatory factors such as IRAP, anti-myostatin proteins, aspartoacylase, monoclonal antibodies (including single chain monoclonal antibodies; an exemplary Mab is the herceptin Mab). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof.

In general, the parvovirus vector can be employed to deliver any heterologous nucleic acid with a biological effect to treat or ameliorate the symptoms associated with any disorder related to gene expression. Alternatively, the invention can be used to treat any disease state for which it is beneficial to deliver a therapeutic polypeptide. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product), diabetes mellitus (insulin), muscular dystrophies including Duchenne (dystrophin, mini-dystrophin, insulin-like growth factor I, a sarcoglycan [e.g., α, β, γ], RNAi against myostatin) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects, congenital emphysema (α1-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1), phospholamban, serca2a, zinc finger proteins that regulate the phospholamban gene, Barkct, β2-adrenergic receptor, β2-adrenergic receptor kinase (BARK), phosphoinositide-3 kinase (PI3 kinase), calsarcin, etc.), arthritis (insulin-like growth factors), joint disorders (insulin-like growth factors), intimal hyperplasia (e.g., by delivering enos, inns), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including RANKL and/or VEGF) can be administered with a bone allograph, for example, following a break or surgical removal in a cancer patient.

Heterologous nucleotide sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Alternatively, the nucleic acid may encode an antisense nucleic acid, a ribozyme (e.g., as described in U.S. Pat. No. 5,877,022), RNAs that effect spliceosome-mediated trans-splicing (see, Puttaraju et al., (1999) Nature Biotech. 17:246; U.S. Pat. No. 6,013,487; U.S. Pat. No. 6,083,702), interfering RNAs (RNAi) including siRNA that mediate gene silencing (see, Sharp et al., (2000) Science 287:2431) or other non-translated RNAs, such as "guide" RNAs (Gorman et al., (1998) Proc. Nat. Acad. Sci. USA 95:4929; U.S. Pat. No. 5,869,248 to Yuan et al.), and the like. Exemplary untranslated RNAs include RNAi against the multiple drug resistance (MDR) gene product (e.g., to treat tumors and/or for administration to the heart to prevent damage by chemotherapy), RNAi against myostatin (Duchenne muscular dystrophy), or RNAi against VEGF (e.g., to treat tumors).

The virus vector may also comprise a nucleic acid that shares homology with and recombines with a locus on the host chromosome. This approach may be utilized to correct a genetic defect in the host cell.

The heterologous nucleic acid can further encode an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccines is known in the art (see, e.g., Miyamura et al, (1994) Proc. Nat. Acad. Sci USA 91:8507; U.S. Pat. No. 5,916,563 to Young et al., U.S. Pat. No. 5,905,040 to Mazzara et al., U.S. Pat. No. 5,882,652, U.S. Pat. No. 5,863,541 to Samulski et al.; the disclosures of which are incorporated herein in their entireties by reference). The antigen may be presented in the parvovirus capsid. Alternatively, the antigen may be expressed from a heterologous nucleic acid introduced into a recombinant vector genome.

An immunogenic polypeptide, or immunogen, may be any polypeptide suitable for protecting the subject against a disease, including but not limited to microbial, bacterial, protozoal, parasitic, fungal and/or viral diseases. For example, the immunogen may be an orthomyxovirus immunogen (e.g., an influenza virus immunogen, such as the influenza virus hemagglutinin (HA) surface protein or the influenza virus nucleoprotein, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, poi and env genes products). The immunogen may also be an arenavirus immunogen (e.g., Lassa fever virus immunogen, such as the Lassa fever virus nucleocapsid protein and the Lassa fever envelope glycoprotein), a poxvirus immunogen (e.g., vaccinia, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and SFS viruses), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogen may further be a polio immunogen, herpes immunogen (e.g., CMV, EBV, HSV immunogens) mumps immunogen, measles immunogen, rubella immunogen, diphtheria toxin or other diphtheria immunogen, pertussis antigen, hepatitis (e.g., hepatitis A, hepatitis B or hepatitis C) immunogen, or any other vaccine immunogen known in the art.

Alternatively, the immunogen may be any tumor or cancer cell antigen. Preferably, the tumor or cancer antigen is expressed on the surface of the cancer cell. Exemplary cancer and tumor cell antigens are described in S. A. Rosenberg, (1999) *Immunity* 10:281). Other illustrative cancer and tumor antigens include, but are not limited to: BRCA1 gene product, BRCA2 gene product, gp100, tyrosinase, GAGE-1/2, BAGE, RAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et al., (1994) *Cancer Res.* 54:3124) including MART-1 (Coulie et al., (1991) *J. Exp. Med.* 180:35), gp100 (Wick et al., (1988) *J. Cutan. Pathol.* 4:201) and MAGE antigen, MAGE-1, MAGE-2 and MAGE-3 (Van der Bruggen et al., (1991) *Science,* 254:1643); CEA, TRP-1, TRP-2, P-15 and tyrosinase (Brichard et al., (1993) *J. Exp. Med.* 178:489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (international patent publication WO 90/05142); telomerases; nuclear matrix proteins; prostatic acid phosphatase; papilloma virus antigens; and antigens associated with the following cancers: melanomas, adenocarcinoma, thymoma, lymphoma, sarcoma, lung cancer, liver cancer, colon cancer, non-Hodgkin's lymphoma, Hodgkin's lymphoma, leukemias, uterine cancer, breast cancer, prostate cancer, ovarian cancer, cervical cancer, bladder cancer, kidney cancer, pancreatic cancer and others (see, e.g., Rosenberg, (1996) *Ann. Rev. Med.* 47:481-91).

Alternatively, the heterologous nucleotide sequence may encode any polypeptide that is desirably produced in a cell in vitro, ex vivo, or in vivo. For example, the parvovirus vectors may be introduced into cultured cells and the expressed gene product isolated therefrom.

It will be understood by those skilled in the art that the heterologous nucleic acids(s) of interest can be operably associated with appropriate control sequences. For example, the heterologous nucleic acid may be operably associated with expression control elements, such as transcription/translation control signals, origins of replication, polyadenylation signals, internal ribosome entry sites (IRES), promoters, enhancers, and the like.

Those skilled in the art will appreciate that a variety of promoter/enhancer elements may be used depending on the level and tissue-specific expression desired. The promoter/enhancer may be constitutive or regulatable, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

The promoter/enhancer element can be native to the target cell or subject to be treated and/or can be native to the heterologous nucleic acid. The promoter/enhancer element is generally chosen so that it will function in the target cell(s) of interest. The promoter/enhancer element can optionally be a mammalian promoter/enhancer element. The promoter/enhance element may further be constitutive or regulatable.

The present invention facilitates the inclusion of regulatable expression control elements in parvovirus vectors, which have previously been restricted because of size limitations. Regulatable promoters/enhancer elements for nucleic acid delivery can be tissue-specific promoter/enhancer elements, and include muscle specific (including cardiac, skeletal and/or smooth muscle), neural tissue specific (including brain-specific), eye (including retina-specific and cornea-specific), liver specific, bone marrow specific, pancreatic specific, spleen specific, and lung specific promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein which the heterologous nucleic acid sequence(s) will be transcribed and then translated in the target cells, specific initiation signals may be required for efficient translation of inserted protein coding sequences. These exogenous translational control sequences, which may include the ATG initiation codon and adjacent sequences, can be of a variety of origins, both natural and synthetic.

There are no particular limits to the size of the heterologous nucleic acid. In particular embodiments, the heterologous nucleic acid is at least about 15, 18, 24, 50, 100, 250, 500, 1000 or more nucleotides long.

The invention also provides pharmaceutical formulations comprising a composition of the invention in a pharmaceutically acceptable carrier. By "pharmaceutically acceptable" is meant a material that is not biologically or otherwise undesirable, i.e., the material may be administered to a subject along with the selected particles, and/or populations thereof, without causing substantial deleterious biological effects or interacting in a deleterious manner with any of the other components of the composition in which it is contained. The pharmaceutically acceptable carrier is suitable for administration or delivery to humans and other subjects of this invention. The carrier would naturally be selected to minimize any degradation of the active ingredient and to minimize any adverse side effects in the subject, as would be well known to one of skill in the art (see, e.g., *Remington's Pharmaceutical Science*; latest edition). Pharmaceutical formulations, such as vaccines or other immunogenic compositions of the present invention can comprise an immunogenic amount of the PIV particles of this invention, in combination with a pharmaceutically acceptable carrier. Exemplary pharmaceutically acceptable carriers include, but are not limited to, sterile pyrogen-free water and sterile pyrogen-free physiological saline solution.

The invention also provides methods of delivering a nucleic acid of interest to a cell, the methods comprising contacting the cell with a parvovirus vector comprising the nucleic acid of interest and a proteasome inhibitor.

As a further aspect, the invention provides methods of delivering a nucleic acid of interest to a subject, the methods comprising administering a parvovirus vector comprising the nucleic acid of interest and a proteasome inhibitor to the subject.

The parvovirus vector and proteasome inhibitor can be administered separately or in the same composition, optionally a pharmaceutical formulation. When administered separately, the parvovirus vector and proteasome inhibitor can optionally be administered concurrently (e.g., within minutes or hours of each other).

The methods of the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, non-human primates bovines, ovines, caprines, equines, felines, canines, lagomorphs, etc. Human subjects include neonates, infants, juveniles, and adults.

Dosages of the parvovirus vectors to be administered to a subject will depend upon the mode of administration, the target tissue or organ, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^3$, $10^{14}$, $10^{15}$ transducing units or more, preferably about $10^6$, $10^7$ or $10^8$ to $10^{12}$ or $10^{13}$ transducing units.

Likewise, the dosage of proteasome inhibitor can be routinely determined, and will vary with the route of administration, the target tissue or organ, the particular proteasome inhibitor, the subject and other parameters that are within the purview of the worker of ordinary skill. In general, the proteasome inhibitor is administered in an amount effective to enhance transduction by the parvovirus vector.

In particular embodiments, more than one administration (e.g., two, three, four or more administrations) of either the vector, the proteasome inhibitor or both, may be employed to achieve the desired level of nucleic acid expression over a period of various intervals, e.g., daily, weekly, monthly, yearly, etc.

Exemplary modes of administration include oral, rectal, transmucosal, topical, intranasal, intrathecal, intraocular, transdermal, inhalation, parenteral (e.g., intravenous, subcutaneous, intradermal, intramuscular [including administration to cardiac, skeletal and/or diaphragm muscle], and intraarticular) administration, and the like, as well as direct tissue or organ injection.

In particular embodiments, the invention is practiced to treat a subject having or at risk for a condition including but not limited to: a muscular dystrophy [including Duchenne or Becker muscular dystrophy], hemophilia A, hemophilia B, multiple sclerosis, diabetes mellitus, Gaucher disease, Fabry disease, Pompe disease, cancer, arthritis, muscle wasting, heart disease [including congenital heart failure or peripheral artery disease], intimal hyperplasia, a neurological disorder [including epilepsy], Huntington's disease, Parkinson's disease or Alzheimer's disease, an autoimmune disease, cystic fibrosis, thalassemia, Hurler's disease, Krabbe's disease, phenylketonuria, Batten's disease, spinal cerebral ataxia, LDL receptor deficiency, hyperammonemia, anemia, arthritis, a retinal degenerative disorder including macular degeneration, adenosine deaminase deficiency, or cancer [including tumor-forming cancers].

Having described the present invention, the same will be explained in greater detail in the following examples, which are included herein for illustration purposes only, and which are not intended to be limiting to the invention.

EXAMPLES

Example 1

Studies with AAV2 and AAV8 Vectors

Delivery of genes that are larger than the wild type adeno-associated virus (AAV) 4680 nucleotide genome is inefficient using AAV vectors. In this study, a 5.6 kb factor VIII expression cassette packaged into AAV was used to test the effect of an FDA-approved proteasome inhibitor (bortezomib) treatment concurrent with vector delivery in vivo. Intrahepatic vector delivery resulted in factor VIII expression that persisted for greater than one year of follow-up in hemophilia mice. A single dose of bortezomib given with AAV2 or AAV8 factor VIII vector enhanced expression on average ~600% and ~300%, respectively. Moreover, co-administration of AAV8.canine FVIII ($1 \times 10^{13}$ vg/kg) and bortezomib in hemophilia A dogs (n=4) resulted in complete normalization of the Whole Blood Clotting Time (WBCT) and 90% reduction in bleeding frequency for up to 32 months compared to untreated hemophilia A dogs (n=3) or dogs administered vector alone (n=3). Validation of phenotypic correction of hemophilia A dogs>than two years by combination therapy of FDA approved drug (bortezomib) and AAV vector carrying over sized transgene facilitates a significant expansion of therapeutic targets in human gene therapy.

Proteasome Inhibitor Bortezomib Dose In Vivo

The primary objective of these studies was to validate in small and large animal "combination therapy" using FDA approved drug bortezomib and AAV transgene vectors. The present studies describe the use of the proteasome inhibitor, bortezomib (also known as Velcade®), as this is the only proteasome inhibitor currently approved for clinical use by the FDA. Bortezomib, like most chemotherapy is dosed based on body surface area. For all large animal studies, the FDA-approved dose of (1.3 mg/m$^2$) was used. However preclinical toxicity data has established a safe bortezomib dose for mice of 0.5 mg per kilogram of body weight[23]. It was established that mice given the 0.5 mg/kg dose without AAV vector tolerated the proteasome inhibitors without apparent side effect or change in hematologic parameters. Additional mice were tested with higher dose (1.0 mg/kg bortezomib), but occasionally mice receiving this dose displayed decreased activity and feeding. Therefore based on prior pre-clinical toxicity studies and analyses, proteasome inhibitor bortexomib was given at 0.5 mg/kg by a single portal vein injection co-administered with the AAV vectors in all mouse studies. Even though the dosing in mice was calculated on a per kilogram body weight basis vs. clinically recommended body surface area, the total dose used in mice is roughly equivalent to total dose used in dog studies described herein.

AAV Vectors and Additional Drugs

The factor VIII expression vector used in these studies has been described previously[6]. The vector contains a canine B domain deleted (BDD) FVIII (cFVIII) cDNA driven by a synthetically derived short liver-specific promoter/enhancer, followed by a chimeric intron (IGBP/enh/intron). The factor IX vector has been described previously and contains a 4.2 kb expression cassette including the hFIX cDNA (1.4 kb) under transcriptional control of CMV enhancer/chicken β-actin promoter (rAAV-CBA-hFIX)[22]. All vectors were produced and titered at the UNC Virus Vector Core Facility as described previously[39], including single strand and self-complementary AAV2 encoding green fluorescent protein (GFP), driven by CMV promoter (total size about 1.5 kb); firefly luciferase encapsidated with AAV8 capsid; driven by CBA promoter; and AAV2 and AAV8 expressing human factor IX(hFIX). Bortezomib (Millennium Pharmaceutical Co, Cambridge, Mass.) was diluted in phosphate buffered saline (PBS) for injection. MG132 (CalBioChem, La Jolla, Calif.) was dissolved with 70% ethanol to 20 mM as stock solution. Dexamethasone was purchased as injectable solution from Sicor Pharmaceuticals Inc, Irvine, Calif.

Cell Culture and FACScan Analysis 293T cells were grown in Dulbecco's modified Eagle's medium (Mediatech, Herndon, Va.) supplemented with 9% fetal bovine serum and 1% penicillin/streptomycin solution and transduced at a multiplicity of infection of 1. At 3-5 days after transduction, cells were harvested, fixed in phosphate-buffered saline (PBS) containing 2% formaldehyde/0.2% glutaraldehyde, and analyzed by FACScan as previously described[40].

Animal Care and Studies

Mice

FVIII deficient mice (FVIII$^{-/-}$) have a targeted deletion of exon 16 of the FVIIII gene. C57Bl/6 FIX$^{-/-}$ mice have a targeted deletion of the promoter through the 3$^{rd}$ exon of the FIX gene. FVIII$^{-/-}$ and FIX$^{-/-}$ mice were bred in house. Wild type C57B6 mice were purchased from the Jackson Laboratory (Bar Harbor, Me.) for luciferase vector delivery at 7-8 weeks of age. Hemophilic mice were anesthetized using 2.5% Avertin for all procedures. All plasma samples were collected from the retro-orbital plexus into 3.2% citrated sodium and stored at −80° C. Retro-orbital blood collection and bioluminescence imaging were performed under isoflurane anesthesia.

FIX$^{-/-}$ mice received portal vein injection of 3×10$^{10}$ gc/animal AAV2.hFIX or AAV8.hFIX vector in a total volume of 200 µl with or without a single dose of bortezomib (0.5 mg/kg) at the time of AAV delivery. FVIII$^{-/-}$ KO mice received portal venous injection of 3×10$^{10}$ gc/mouse AAV2.cFVIII or AAV8.cFVIII, along with bortezomib or MG132 (0.5 mg/kg body weight), as well as a single dose of 1 mg/kg of recombinant human factor VIIa (NovoSeven, Novo Nordisk, Denmark) to support perioperative hemostasis. To avoid anticipated antibody-mediated immune responses to the canine FVIII transgene, all FVIII$^{-/-}$ mice received cyclophosphamide (Sigma Aldrich, St Louis, Mo.) injected intraperitoneally in 3 doses of 100 µg each on days −3, 0, and +3, as previously described[5].

C57B6 mice received 10$^{11}$ vector genomes/mouse AAV8 expressing firefly luciferase under transcriptional control of CMV enhancer/chicken β-actin promoter via tail vein; groups receiving dexamethasone therapy were treated with 0.2 mg/animal intraperitoneally 1-2 hours prior to AAV delivery.

Animal Care and Studies

Hemophilia A Dogs

The hemophilia A dogs were mixed breed dogs from the hemophilia A colony initially housed at the Scott-Ritchey Research Center, Auburn University but now at the UAB Medical School. All animals were housed in facilities that are AAALAC accredited. Treated dogs were males (n=4) or females (n=3) with severe hemophilia A. All 7 dogs were administered AAV8.cFVIII by mesenteric vein administration 3-4 weeks following birth[41]. Four dogs (2 female/2 male) were also administered bortezomib (1.3 mg/m$^2$) at the time of vector administration. One male and one female dog were administered IV dexamethasone (1.0 mg/kg) at the time of vector and bortezomib administration.

Coagulation Factor VIII and Factor IX Activity Assays and Canine Factor VIII Bethesda Inhibitor Antibody Assay in Mice Canine FVIII activity in mouse plasma was measured by the Coatest SP4 kit (Chromogenix, DiPharma, West Chester, Ohio) following the manufacture's instruction with modification. Normal canine plasma (regarded as 100 percent activity=1 IU/ml) was serially diluted into FVIII$^{-/-}$ pooled mouse plasma to generate the standard curve. Neutralizing antibodies to canine FVIII in mouse were measured by the Bethesda assay using a START 4 Coagulation Analyzer as described[42] (Diagnostica Stago, Asnières, France). Human factor IX was measured based on one-stage factor IX activity assay (FIX-specific aPTT) as previously described, using a START 4 Coagulation Analyzer (Diagnostica Stago, Asnières, France)[43].

FVIII Activity, Coagulation and Bethesda Assays in Dogs

Blood samples were obtained from normal controls, untreated FVIII controls and treated hemophilia A dogs as described[44]. The whole blood clotting time (WBCT) and Bethesda titer were measured as previously described. The WBCT assay was terminated at 20 minutes if a clot had not formed.

Preparation of Hepatic Cell Nuclear and Cytoplasmic Extract

Nuclear and cytoplasmic fractions were isolated as described[45] with slight modification. Mouse livers were perfused with phosphate buffered saline (PBS) and minced on ice and homogenized (buffer: 250 mM sucrose, 50 mM Tris-HCl (pH 7.5), 25 mM KCl, 5 mM MgCl$_2$, 0.5% NP-40, 1 mM phenylmethylsulfonyl fluoride (PMSF)), using a Dounce homogenizer. Nuclei and other organelles were collected by centrifugation for 10 min at 3,000 rpm in a Sorvall clinical centrifuge. The supernatant was filtered using a 40-µm-pore-size filter and used as the cytoplasm. The multilayered pellet was processed further into nuclear extract dissolved into distilled water.

In Vivo Bioluminescence Imaging

One week after injection of AAV8.luciferase vector, mice were injected intraperitoneally with 150 µg/g D-luciferin (Biotium, Hayward, Calif.) in PBS. Bioluminescence imaging with a CCD camera (IVIS, Xenogen) was initiated exactly 15 min after injection. Signal intensities from live whole body imaging is expressed as total photon flux (photons/s/cm$^2$).

Quantitative PCR (Q-PCR) of Canine Factor VIII and of Firefly Luciferase Transgenes Q-PCR for cFVIII DNA was performed on genomic DNA isolated from mouse liver[11] using iQ SYBR Green kit from Bio-Rad (Hercules, Calif.) at two weeks after factor VIII vector delivery. The copy number of cFVIII DNA was quantified against standards generated with linearized plasmid encoding canine BDD FVIII DNA serially diluted in pooled genomic DNAs from naive C57 mice, from 1×10$^7$ to 1 copy/reaction and normalized for mouse β-actin. The primer sequences used for canine FVIII were identical to those previously described[11,17]. Q-PCR for luciferase DNA was performed at one week after luciferase vector delivery. Following bioluminescence imaging, the mice were sacrificed and genomic DNA was extracted from liver, brain, heart, lung, spleen, stomach, kidney, ileum, muscle, and testis. Q-PCR of luciferase and beta actin was performed on genomic DNAs isolated using iQ SYBR Green kit from Bio-Rad (Hercules, Calif.). The copy numbers of luciferase and canine FVIII gene products were quantified and normalized for mouse β-actin and expressed as vector copies per cell. All Q-PCR reactions were performed on iCycler (Bio-Rad Laboratories, Hercules, Calif.).

Figure 2A:
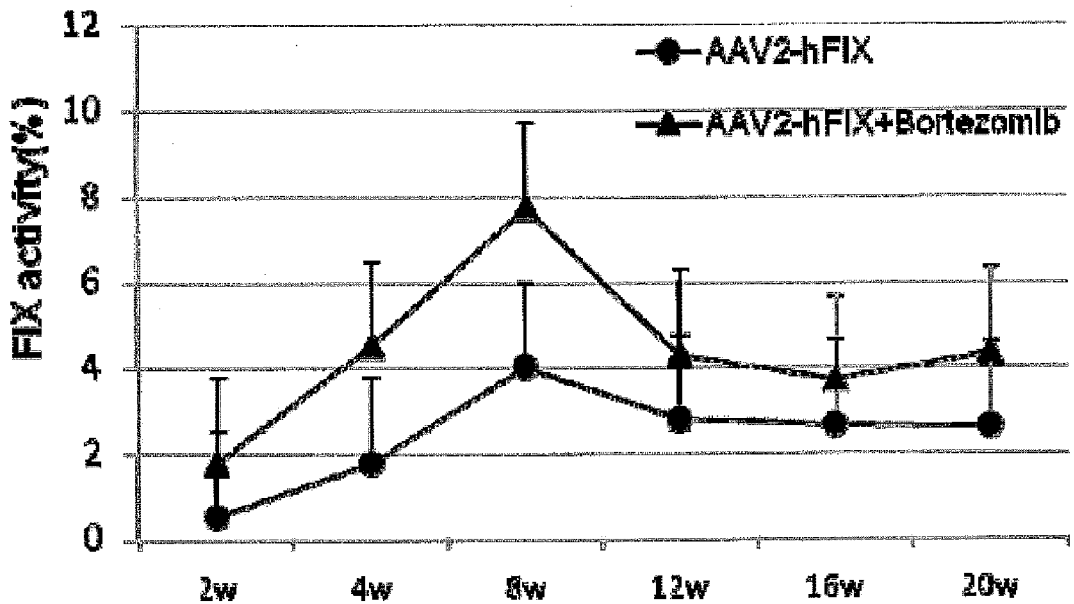
FIGS. 2A-D. Effect of proteasome inhibitor co-administration with AAV2 and AAV8 vectors for the correction of factor IX deficient and factor VIII deficient mice. Hemophilic mice received $3 \times 10^{10}$ vector genomes/mouse of single AAV2 or AAV8 vectors with or without proteasome inhibitor (0.5 mg/kg body weight) co-administered to the portal vein. (A) and (B) Percent of normal human factor IX activity in FIX$^{-/-}$ mice following AAV2 (a) or AAV8 (b) with or without bortezomib. (C) and (D) Percent of normal canine factor VIII activity (Coatest assay) in FVIII$^{-/-}$ mice following AAV2 (c) or AAV8 (d) in the absence of presence of proteasome inhibitors MG-132 and bortezomib. Data are presented as mean±SD. * Bortemozib vs. AAV-cFVIII control, P<0.05; ** Bortemozib vs. MG-132 and AAV-cFVIII control, P<0.05.
Figure 2B:
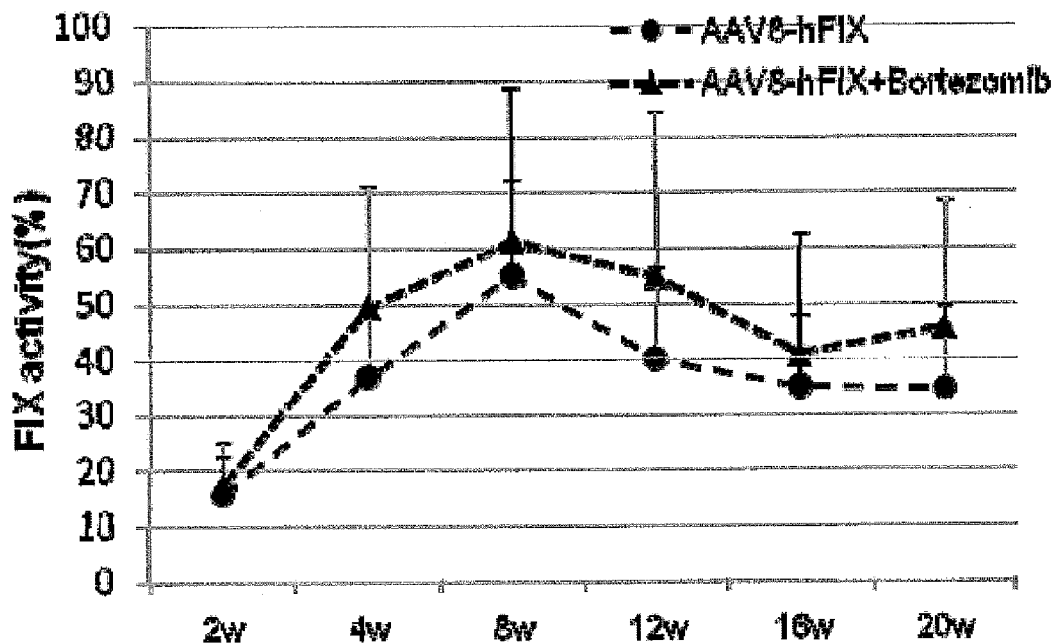

Proteasome Inhibitor Effect on AAV Serotypes Carrying Wild Type Size Factor IX Expression Cassette in Hemophilia B Mice Studies were conducted to test the effect of combination therapy using bortezomib on in vivo correction of hemophilic animals. First, a vector carrying a genome approximately the same size as wild type AAV was used for the correction of hemophilia B in a mouse model. AAV vectors carrying a human factor IX expression cassette driven by the CMV enhancer/Chicken β-actin promoter, described previously[22], was infused via the portal vein to hemophilia B mice with or without a single dose of bortezomib at the time of the vector delivery. As shown in FIG. 2A, ssAAV2.FIX-treated mice averaged 2.4% factor IX activity over the 20 weeks of observation. Bortezomib treatment resulted in an average expression of 4.3% factor IX over the same period, equivalent to an 83% increase in factor IX expressed. Liver-directed factor IX expression was more efficient using AAV8 than AAV2, and mice receiving vector alone expressed on average 40% factor IX activity over the 20 weeks. Factor IX expression over 20 weeks was modestly augmented in mice receiving the single dose of bortezomib co-administered with the AAV8 vector, averaging ~24% higher factor IX activity (FIG. 2B).

Proteasome Inhibitor Effect on AAV Serotypes Carrying Larger than Wild Type Size cFVIII Expression Cassette in Hemophilia A Mice Studies were carried out to analyze the effect of combination therapy using large transgene cassette FVIII in hemophilic A mice using the same genetic background (C57Bl/6). The Factor VIII cDNA (~7.1 kb) contains a large B domain (~2.7 kb) that does not contribute to blood clotting; once the majority of sequences coding for the B-domain are removed, the cFVIII cDNA sequence of 4.5 kb can be incorporated in AAV vectors. Nevertheless, after the addition of promoter and other required transcriptional regulatory elements these vectors produce an oversized AAV expression cassette of 5.6 kb. AAV2 and AAV8 vectors were generated using the 5.6 kb FVIII expression plasmid. Virus was characterized for total particle number by qPCR, virion integrity by electron microscopy, capsid ratio by silver stain, and DNA genome size by alkaline gel electrophoresis. All vector parameters were consistent between multiple production runs for both mouse and canine studies with previous studies. For FVIII studies, the proteasome inhibitors MG-132 (also called Z-LLL) and bortezomib were chosen so that MG-132 could be compared with the clinically approved but untested agent, bortezomib.

Figure 2C:
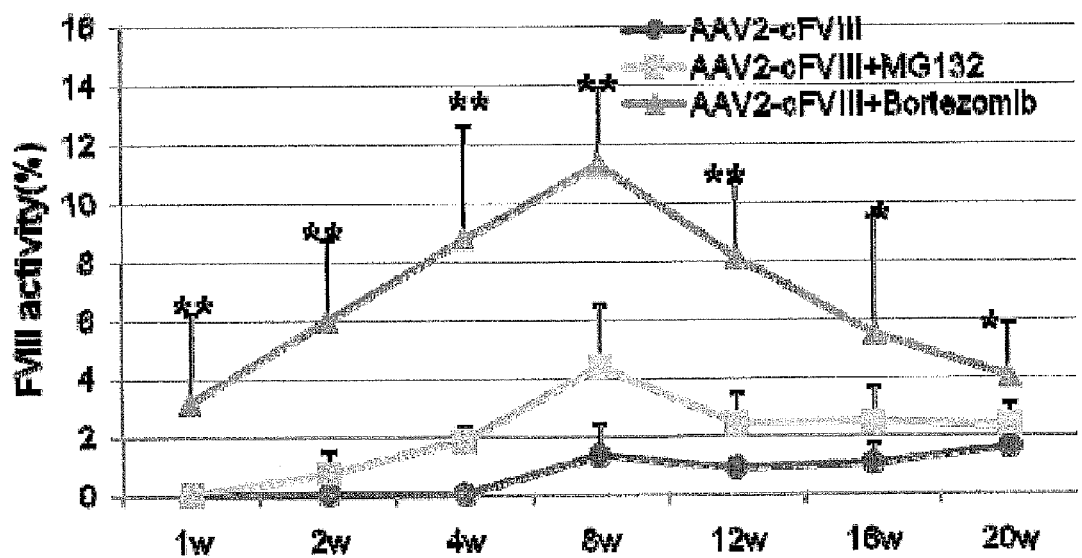
Figure 2D:
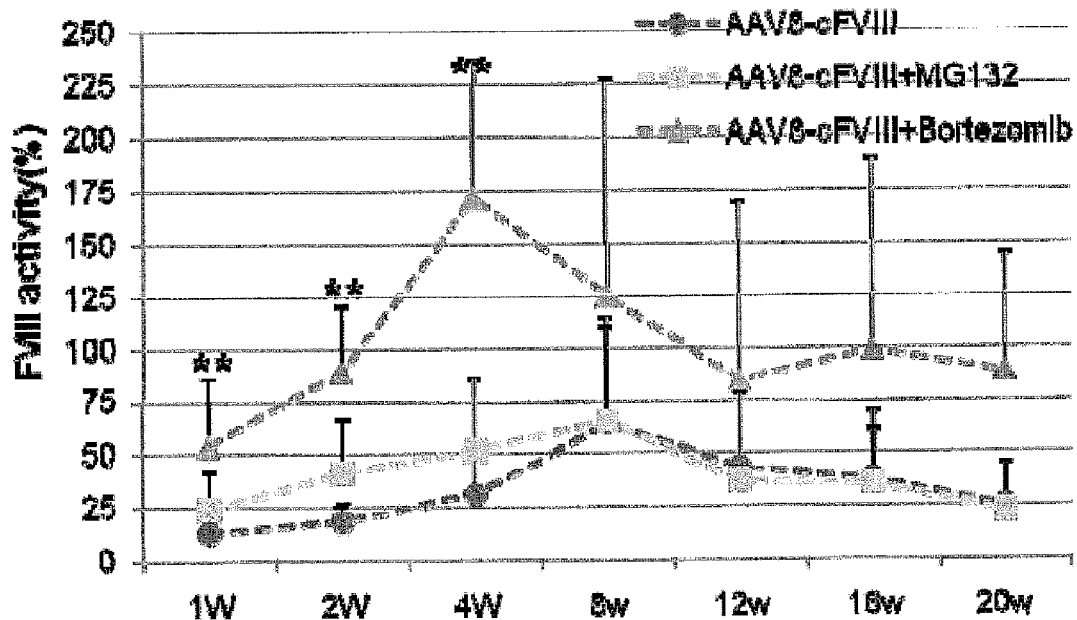

Both MG-132 and bortezomib led to increased FVIII transgene expression compared to mice receiving vector alone (FIGS. 2C, and 2D). As shown in FIG. 2C, FVIII activity was undetectable until week 8 after AAV2 vector alone, while factor VIII was detectable at week 2 in mice receiving co-administration of MG132 and at week 1 in mice that received bortezomib. Expression was increased on average >150% by MG132 and >550% bortezomib.

In contrast to the delayed onset of expression observed in mice receiving AAV2 vector without proteasome inhibitor, mice receiving the AAV8 vector alone (FIG. 2D) had canine FVIII detectable at the earliest examination at week one after transduction. In these mice, canine factor VIII peaked at 8 weeks, then began to decrease. Although slightly increased factor VIII expression was observed in the first month after AAV8 with the co-administration of MG-132, the improvement of factor VIII expression was not as significant or persistent as was observed using bortezomib. Bortezomib co-administration improved initial and sustained canine factor VIII expression. On average, factor VIII expression was 259% higher in mice receiving the single dose of bortezomib when compared to mice receiving AAV8.cFVIII vector alone. Analysis of liver alanine aminotransferase (ALT) and aspartate aminotransferase (AST) and complete blood counts did not show any evidence of hepatic or hematologic toxicity in any mice receiving vector alone or in combination with bortezomib. To facilitate comparison of the proteasome inhibitor effect upon vectors generated from wtAAV-sized factor IX transgene and oversized factor VIII transgene, the same time points are graphed in FIGS. 2A and 2B (factor IX) and FIGS. 2C and 2D (factor VIII). Bortezomib treatment was associated with a proportionately greater augmentation of the oversize transgene expression than that of the smaller transgene. This result corroborated in vitro studies using identical (chloramphenicol acetyltransferase gene-CAT) or heterologous (CFTR) transgene cassettes[3].

Proteasome Inhibitor Increase Nuclear Accumulation of Genomes In Vivo

Hemophilia A mice were next treated with a combination therapy of factor VIII vector and proteasome inhibitor and the abundance of vector sequences in the cytoplasm and nuclear compartment were compared. Two weeks after vector administration with or without bortezomib, total liver cell cytoplasmic and nuclear fractions from AAV8.FVIII-treated mice were purified and examined to determine the location of intracellular accumulation of vector genomes. The ratio of genomes persisting in the nucleus rather than cytoplasm was increased by the single dose of bortezomib, supporting a role in influencing viral infection. These results suggest a pathway that may divert oversized vector genomes from cytoplasm to nuclear structures for subsequent steps in vector uncoating and/or genome complementation as suggested by recent reports (Table 1).

Figure 3:
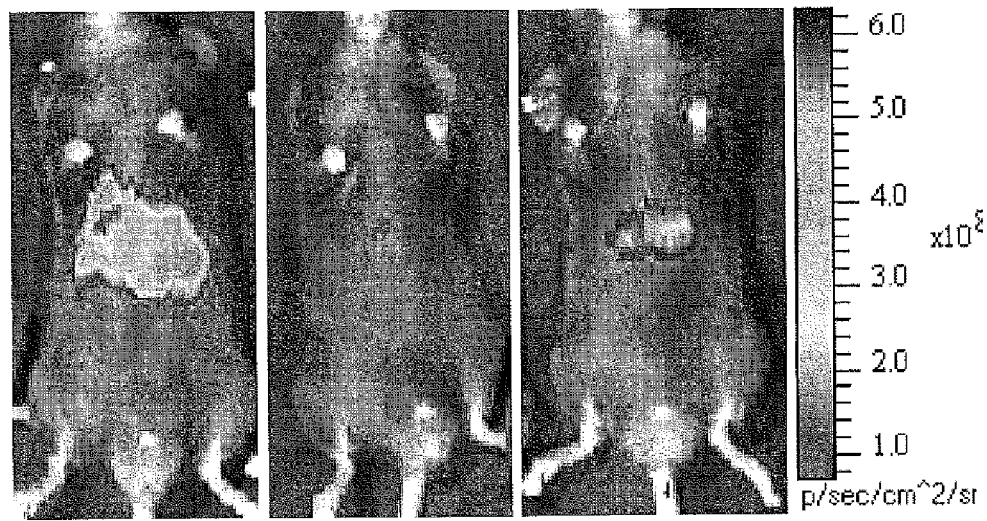
FIG. 3. Hepatosplenic localization of AAV.Luciferase expression by co-administered dexamethasone. C57B6 mice were injected via tail vein with $10^{11}$ genome/mouse of AAV8.Luciferase with or without co-administration of 0.2 mg I.V. dexamethasone. One week later whole body living bioluminescence imaging was obtained and signal intensity is expressed as total photon flux (photons/s/cm$^2$).
Figure 3:
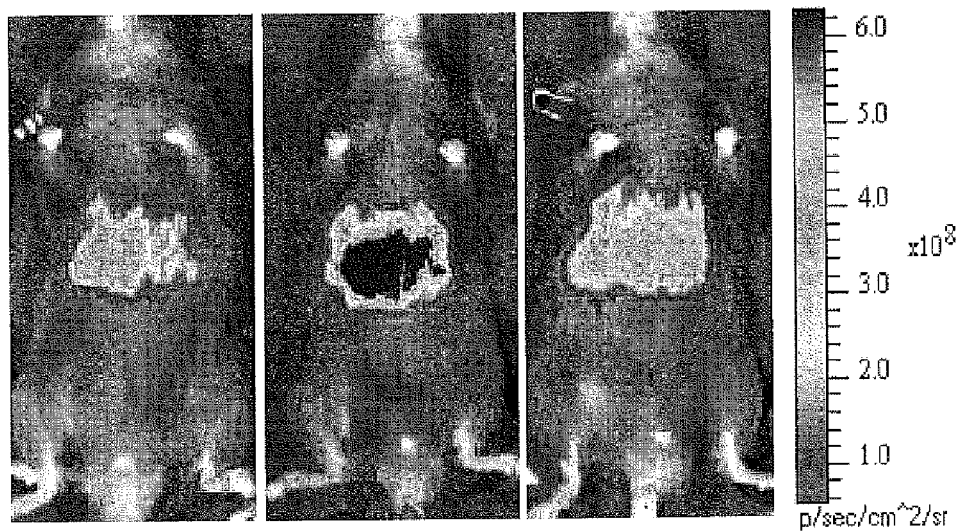

Dexamethasone Reduces Ectopic AAV Vector Scatter to Increase Proportional Hepatic Transduction During Liver-Directed Gene Therapy Bortezomib and dexamethasone are commonly used together in clinical oncology therapies. Compared with bortezomib therapy alone, the combination of dexamethasone and bortezomib has increased efficacy, as has the addition of dexamethasone in the setting of incomplete clinical response to bortezomib monotherapy.[24][25][26] To determine if this clinical parameter is also important for enhanced vector transduction of oversized transgene cassettes, the outcome of vector transduction in multi-drug combination therapy was evaluated. Previous studies were carried out to examine some additional pharmacologic agents in an effort to decrease the uptake of AAV vectors expressing reporter gene at ectopic sites during liver directed gene therapy. During these early studies, a trend to decrease ectopic vector scatter was observed when dexamethasone was co-administered with vector. This was reflected in lower gene expression and genome persistence in several organs, including heart, spleen, and pancreas with a modest increase in hepatic delivery (FIG. 3 and Table 2). Based on clinical use of dexamethasone with bortezomib, and these results, studies were carried out in which an additional group of AAV8.cFVIII/bortezomib mice were treated simultaneously with a single dose of the corticosteroid dexamethasone and the effect on persistent transgene expression was examined.

Figure 4:
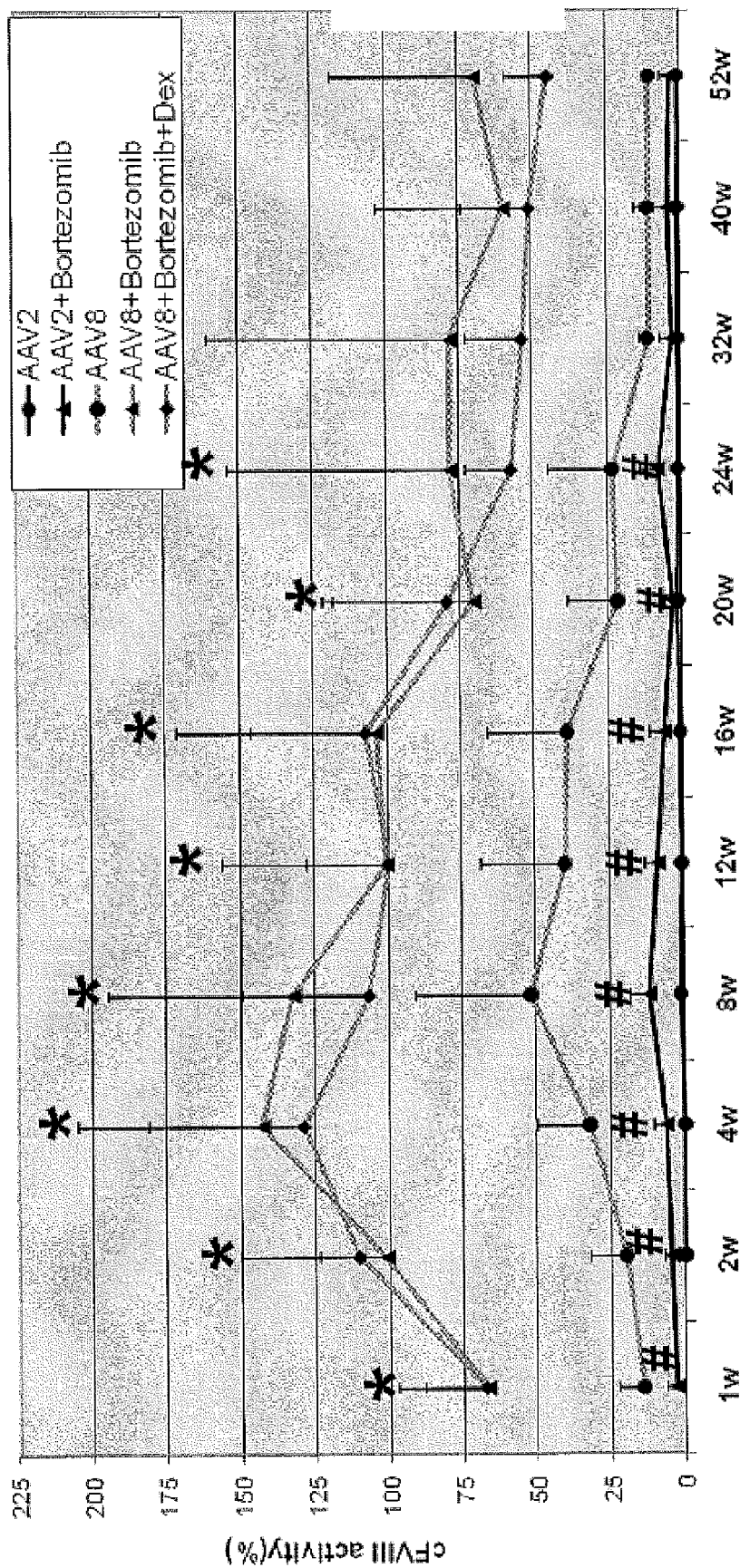
FIG. 4. Persistent effect of single-dose bortezomib on AAV2- and AAV8-mediated cFVIII expression in hemophilia A mice. FVIII$^{-/-}$ mice were injected with AAV2 or AAV8 expressing cFVIII at a dose of $3 \times 10^{10}$ gc/mouse, without PI or with bortezomib (0.5 mg/kg body weight) or bortezomib plus dexamethasone (0.2 mg/animal, equivalent to 8 mg/kg body weight) by portal vein injection. Citrated plasma was collected at defined time points for FVIII activity detected by Coatest assay. Data are presented as mean±SD in % activity of normal canine activity. * AAV8.cFVIII+Bortezomib (with or without dexamethasone) vs. AAV8.cFVIII vector alone, P<0.05. #AAV2.cFVIII+Bortezomib vs. AAV2.cFVIII vector alone, P<0.05.

Long-Term Observation of Pharmacologic Enhancement of AAV.cFVIII Expression in FVIII Knockout Mice Having established the potential of bortezomib to enhance factor VIII expression, additional mice were treated with AAV2 and AAV8 vectors to determine the duration of bortezomib enhancement. Circulating factor VIII activity in mice receiving AAV2 alone was first detectable at 8 weeks, and fluctuated around the lower limit of detection of this assay (~1% activity=0.01 IU/ml) throughout one year of observation (FIG. 4) However, co-administration of bortezomib resulted in detectable factor VIII activity at week 1 in most mice, which peaked at week 8 (0.11±0.06 IU/ml) and was maintained at more than 3% for a year. Expression of cFVIII from the AAV8 vector peaked at week 8 (0.51±0.38 IU/ml) before gradually decreasing to a plateau ~10% of normal human factor VIII activity that was maintained to week 52 (the final observation, 0.10±0.019 IU/ml). In contrast, mice treated with AAV8.cFVIII and the single dose of bortezomib exceeded even at the first timepoint (week 1) the peak value of the vector-only group, and maintained cFVIII activity of >50% normal throughout one year of observation (cFVIII activity 0.67±0.58 IU/ml at week 52), as shown in FIG. 4. In these studies the overall pattern of expression in bortezomib-treated mice was similar with and without the addition of dexamethasone.

Development of Canine FVIII-Neutralizing Antibodies in FVIII Knockout Mice

As shown in Table 3, some mice in each of the treatment groups developed FVIII-neutralizing antibodies at various times 2-20 weeks after vector exposure, despite cyclophosphamide dosing performed per the schedule outlined by Sarkar et al.[6] Inhibitor titers were near the lower limits of detection in the few AAV2.cFVIII-treated mice that developed antibodies, and the significance of these borderline titers is unclear. As previously reported by Jiang et al, [16] inhibitors developed more frequently with AAV8.cFVIII than with AAV2.cFVIII, being seen in 6/10 mice receiving AAV8.cFVIII without proteasome inhibitor. Co-administration of bortezomib appeared to decrease the incidence of inhibitor formation in animals treated with AAV8 serotype (5/15 mice, 33.3%). The combination of corticosteroid and bortezomib was associated with the lowest rate of inhibitor formation (20% of AAV8.cFVIII/bortezomib/dexamethasone mice vs. 60% of vector-only mice), suggesting potential benefit from this combination therapy.

Phenotypic Improvement of Hemophilia A Dogs Given Bortezomib Concurrently with AAV Vector Using identical AAV cFVIII vector cassettes, studies were carried out to determine whether proteasome inhibitor augmentation of the expression of large transgenes translates to the canine hemophilia A model. As shown in Table 4, a total of seven hemophilia A dogs were treated with AAV8.cFVIII with follow-up of at least ten months (longest follow-up=32 months). Three hemophilia A pups received a limiting dose of $1 \times 10^{13}$ vg/kg AAV8.cFVIII (AAV8) via the portal vein. Four hemophilia A pups received the same AAV therapy and received a single I.V. dose of the proteasome inhibitor bortezomib at FDA-approved dose of (1.3 mg/m$^2$). The vector and proteasome inhibitor were well tolerated. Specifically, no liver transaminase elevations, neurologic symptoms or changes in hematologic parameters were observed.

Figure 5:
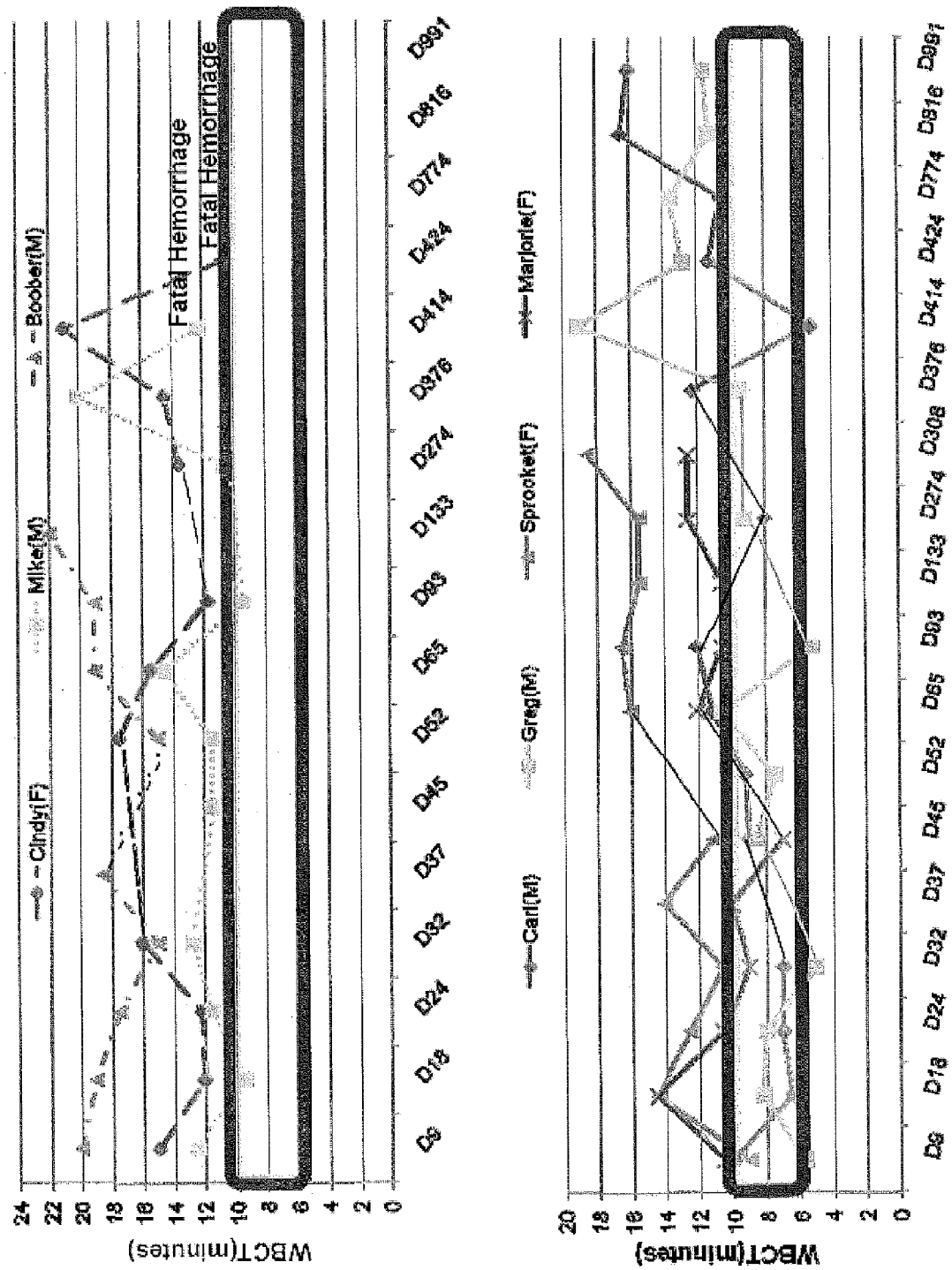
FIG. 5. Persistent effect of proteasome inhibitor therapy on correction of coagulation by liver-directed AAV8-mediated cFVIII gene therapy in hemophilia A dogs. Top: Whole Blood Clotting Time (WBCT) in 2 male and 1 female hemophilia A dogs treated with vector only and no bortezomib. Bottom: WBCT in 2 male and 2 female hemophilia A dogs treated with co-administration of a single dose of intravenous (I.V.) bortezomib at the time of AAV vector administration. Normal range of 6-10 minutes for hemostatically normal dogs is indicated by the shaded region. Hemophilic dogs had baseline WBCT prolonged at greater than 20 minutes.

Correction of plasma clotting potential was quantified using the Whole Blood Clotting Time (WBCT). The time to clot in hemostatically normal dogs is a WBCT of 6-10 minutes; the WBCT in untreated hemophilia A dogs is greater than 20 minutes. Examining the potential effect of combination therapy at the earliest timepoint, the mean WBCT at one week after delivery of AAV8 alone was >16 minutes, as compared to 8.8 minutes in dogs receiving bortezomib+AAV8 (FIG. 5 and Table 4). Remarkably, the effect of the single dose of bortezomib was evident for months. Examining correction during the first ten months following vector delivery (the minimum amount of follow-up that is available for all seven dogs), the two male dogs receiving AAV8 alone had only 4 of a total of 40 (10%) individual WBCT measurements in the normal range; males getting bortezomib AAV8 had 33 of 44 (75%) individual WBCT assays completely normalized during the same period of observation. Liver transduction using AAV2 and AAV8 gene therapy vectors has been reported previously to be less efficient in females than in males[11,29]. Female dogs receiving bortezomib+AAV8 had 12 of 40 (30%) individual WBCT measurements corrected into the normal range over ten months of follow-up; a female getting vector without PI had only 1 of 20 (5%) of WBCT values in the normal range.

Importantly, the combination therapy augmentation of plasma clotting potential translated directly into correction of the bleeding phenotype (Table 4). This strain of hemophilia A dogs typically experiences bleeds about 6 times/year. Three age-matched untreated hemophilic dogs from the same colony bled 10, 10 and 13 times each during 22 months observation concurrent with this study, resulting in a monthly bleeding rate of 0.50±0.08 hemorrhages/month. The dogs receiving AAV8.FVIII vector alone had a mean bleeding frequency of 0.80±0.26 bleeds/month, not significantly different from untreated hemophilic dogs (P=0.23). Dogs that received bortezomib with vector had a mean of 0.07±0.08 hemorrhages/month, which was a striking improvement compared to matched, untreated hemophilic dogs (P<0.0001) and vector-only treated dogs (P<0.003). The original treatment group (n=4) has now been followed for more than 32 months. Bortezomib+vector dogs have had 1 and 2 spontaneous bleeds, respectively. During the same period, the vector only dogs had 12 and 16 bleeds before each experiencing a fatal hemorrhage at 16 and 25 months after vector treatment, respectively.

Correction of hemophilia A through gene therapy remains a goal of modern medicine. Strategies using AAV vectors are attractive, but delivery of factor VIII cDNA has thus far been limited since it exceeds the packaging capacity of wt AAV. AAV vectors carrying oversize transgene cassettes have been demonstrated to transduce cells less efficiently. This inefficiency can be overcome significantly by use of pharmacological agents such as proteasome inhibitors[3]. These studies indicate that concurrent administration of FDA approved proteasome inhibitor bortezomib with AAV vector may improve persistent correction of diseases requiring expression of a large transgene.

These studies also demonstrate that the expression of an oversized factor VIII cDNA delivered by AAV can be enhanced several fold in hemophilic mice and dogs. The enhanced expression was demonstrated using two different serotype AAV vectors. The effect persisted in vivo without further proteasome treatment (>1 year in hemophilic mice and >2 and ½ years in hemophilic dogs). Most importantly, in the hemophilia A dogs the single dose proteasome inhibitor therapy safely augmented a limiting AAV vector dose, which was not able to correct the disease phenotype in the absence of drug. As a result, only the dogs receiving bortezomib "combination therapy" demonstrated persistent protection from the chronic recurrent and lethal bleeding complications of severe factor VIII deficiency.

In studies aimed at characterizing AAV vectors having either a conventional single-strand (ssAAV) or a self-complementing genome structure (scAAV), an increase in the percentage of cells expressing transgene after AAV2.GFP transduction and bortezomib co-administration was observed (FIG. 1). In vitro, the amount of fluorescence from the population of successfully transduced cells was augmented to an even greater degree (from a mean fluorescence index of 75 to 890). The bortezomib augmentation of expression from a self-complementing vector was almost identical to that seen with ssAAV suggesting a common pathway regardless of vector template conformation.

Example 2

Further Studies with AAV Vectors

Figure 6:
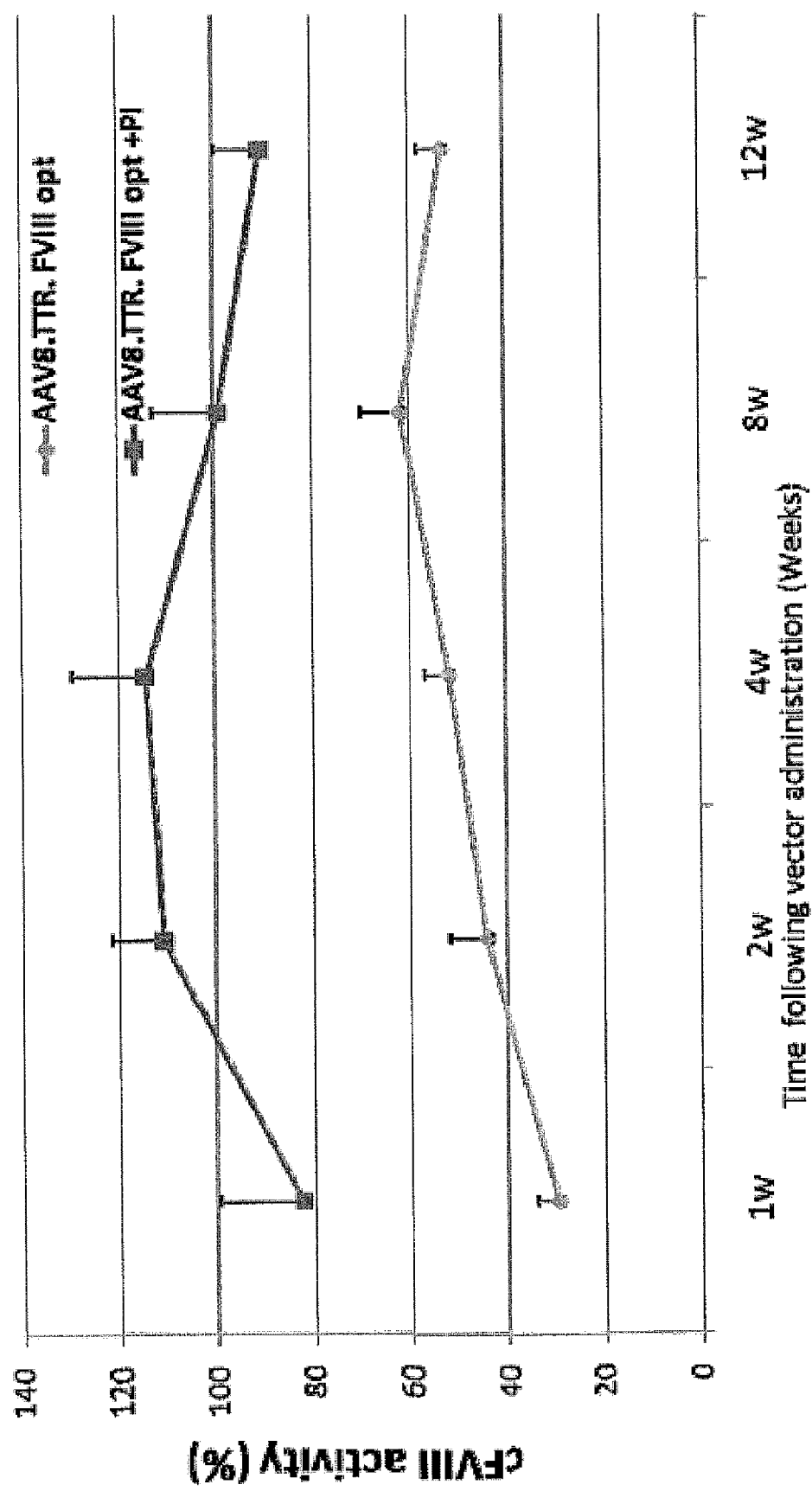
FIG. 6. Expression from AAV.factor VIII vector having a codon-optimized FVIII cDNA is further augmented by the coadministration of proteasome inhibitor bortezomib (PI) at vector delivery.

Factor VIII$^{-/-}$ mice received $3 \times 10^{10}$ vg/animal single strand AAV serotype 8 vector encoding an oversized factor VIII transgene (n=5 mice per treatment group). The canine factor VIII cDNA sequence incorporated in the vector was engineered for optimal mammalian codon usage and GC nucleotide content. Mice received vector infusion to portal vein either alone or in combination with 0.5 mg/kg of proteasome inhibitor bortezomib (PI). While it has been established that codon-optimization increases expression from clotting factor VIII and IX vectors, it was not established whether PI could further augment the more efficient codon-optimized vectors. The augmented expression of codon-optimized factor VIII following the single administration of bortezomib (FIG. 6, upper line), persisted throughout the length of the study (12 weeks).

Figure 7:
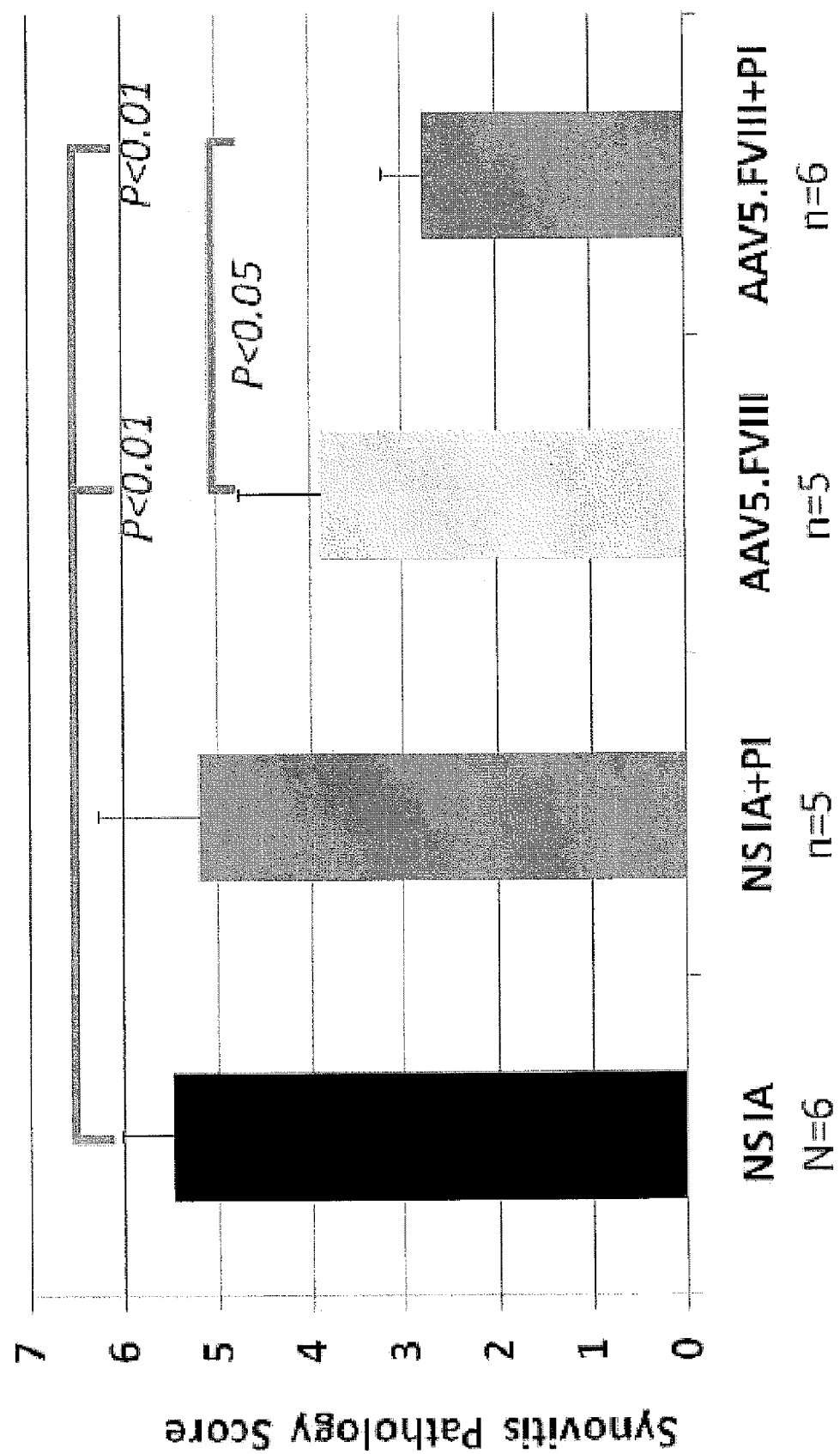
FIG. 7. Coadministration of proteasome inhibitor with AAV in the intraarticular space results in greater therapeutic action of expressed factor VIII to prevent bleeding-induced damage to joints. NSIA: normal saline intraarticular injection.

Hemophilic FVIII$^{-/-}$ mice that received treatment of hindlimb knee joint with either normal saline (NS) with or without proteasome inhibitor bortezomib (PI) 0.5 mg/kg I.V. were not protected from developing destructive synovitis when subjected to a subsequent knee injury (synovitis score>5). Mice receiving treatment with AAV serotype 5 encoding an oversized transgene Factor VIII vector and subsequently injured were partially protected from pathologic changes (synovitis score 3.89±0.86), but coadministration of PI with the AAV5.FVIII resulted in the greatest protection from subsequent injury (synovitis score 2.77±0.45) (FIG. 7). Additionally, when synovial fluid is lavaged from the joints of the mice that receive AAV5.FVIII, factor VIII activity cannot be detected within the levels of sensitivity of the one-stage factor VIII activity assay (<1% factor VIII). However, synovial fluid from mice treated with PI at the time of AAV5.FVIII delivery has measurable factor VIII activity (1.1-2.3% activity).

The foregoing is illustrative of the present invention, and is not to be construed as limiting thereof. The invention is defined by the following claims, with equivalents of the claims to be included therein.

All publications, patent applications, patents, nucleotide sequences, amino acid sequences (e.g., as identified by GenBank® Database Accession numbers and other references cited herein are incorporated by reference in their entireties for the teachings relevant to the sentence and/or paragraph and/or table in which the reference is presented.

REFERENCES

1. Allocca, M., et al. Serotype-dependent packaging of large genes in adeno-associated viral vectors results in effective gene delivery in mice. *J Clin Invest* 118, 1955-1964 (2008).
2. Dong, J. Y., Fan, P. D. & Frizzell, R. A. Quantitative analysis of the packaging capacity of recombinant adeno-associated virus. *Hum Gene Ther* 7, 2101-2112 (1996).
3. Grieger, J. C. & Samulski, R. J. Packaging capacity of adeno-associated virus serotypes: impact of larger genomes on infectivity and postentry steps. *J Virol* 79, 9933-9944 (2005).
4. Hermonat, P. L., Quirk, J. G., Bishop, B. M. & Han, L. The packaging capacity of adeno-associated virus (AAV) and the potential for wild-type-plus AAV gene therapy vectors. *FEBS Lett* 407, 78-84 (1997).
5. Lu, H., et al. Complete correction of hemophilia A with adeno-associated viral vectors containing a full-size expression cassette. *Hum Gene Ther* 19, 648-654 (2008).
6. Sarkar, R., et al. Total correction of hemophilia A mice with canine FVIII using an AAV 8 serotype. *Blood* 103, 1253-1260 (2004).
7. Chao, H., Sun, L., Bruce, A., Xiao, X. & Walsh, C. E. Expression of human factor VIII by splicing between dimerized AAV vectors. *Mol Ther* 5, 716-722 (2002).
8. Chen, L., et al. The enhancing effects of the light chain on heavy chain secretion in split delivery of factor VIII gene. *Mol Ther* 15, 1856-1862 (2007).
9. Zhang, L., et al. Efficient expression of CFTR function with adeno-associated virus vectors that carry shortened CFTR genes. *Proc Natl Acad Sci USA* 95, 10158-10163 (1998).
10. Wang, B., Li, J. & Xiao, X. Adeno-associated virus vector carrying human minidystrophin genes effectively ameliorates muscular dystrophy in mdx mouse model. *Proc Natl Acad Sci USA* 97, 13714-13719 (2000).
11. Wu, Z., et al. Optimization of self-complementary AAV vectors for liver-directed expression results in sustained correction of hemophilia B at low vector dose. *Mol Ther* 16, 280-289 (2008).
12. Douar, A. M., Poulard, K., Stockholm, D. & Danos, O. Intracellular trafficking of adeno-associated virus vectors: routing to the late endosomal compartment and proteasome degradation. *J Virol* 75, 1824-1833 (2001).
13. Duan, D., Yue, Y., Yan, Z., Yang, J. & Engelhardt, J. F. Endosomal processing limits gene transfer to polarized airway epithelia by adeno-associated virus. *J Clin Invest* 105, 1573-1587 (2000).
14. Landowski, Megli, C. J., Nullmeyer, K. D., Lynch, R. M. & Dorr, R. T. Mitochondrial-mediated disregulation of Ca2+ is a critical determinant of Velcade (PS-341/bortezomib) cytotoxicity in myeloma cell lines. *Cancer Res* 65, 3828-3836 (2005).
15. Ponder, K. P. Gene therapy for hemophilia. *Curr Opin Hematol* 13, 301-307 (2006).

16. Jiang, H., et al. Multiyear therapeutic benefit of AAV serotypes 2, 6, and 8 delivering factor VIII to hemophilia A mice and dogs. *Blood* 108, 107-115 (2006).
17. Sarkar, R., et al. Long-term efficacy of adeno-associated virus serotypes 8 and 9 in hemophilia a dogs and mice. *Hum Gene Ther* 17, 427-439 (2006).
18. Scallan, C. D., et al. Sustained phenotypic correction of canine hemophilia A using an adeno-associated viral vector. *Blood* 102, 2031-2037 (2003).
19. Jennings, K., et al. Proteasome inhibition enhances AAV-mediated transgene expression in human synoviocytes in vitro and in vivo. *Mol Ther* 11, 600-607 (2005).
20. Johnson, J. S. & Samulski, R. J. Enhancement of adeno-associated virus infection by mobilizing capsids into and out of the nucleolus. *J Virol* 83, 2632-2644 (2009).
21. Nathwani, A. C., et al. Enhancing transduction of the liver by adeno-associated viral vectors. *Gene Ther* (2008).
22. Jin, Zhang, T. P., Gui, T., Stafford, D. W. & Monahan, P. E. Creation of a mouse expressing defective human factor IX. *Blood* 104, 1733-1739 (2004).
23. LeBlanc, R., at al. Proteasome inhibitor PS-341 inhibits human myeloma cell growth in vivo and prolongs survival in a murine model. *Cancer Res* 62, 4996-5000 (2002).
24. Jagannath, S., at al. Bortezomib therapy alone and in combination with dexamethasone for previously untreated symptomatic multiple myeloma. *Br J Haematol* 129, 776-783 (2005).
25. Sood, R., et al. Retreatment with bortezomib alone or in combination for patients with multiple myeloma following an initial response to bortezomib. *Am J Hematol* 84, 657-660 (2009).
26. Harousseau, J. L., et al. Bortezomib plus dexamethasone as induction treatment prior to autologous stem cell transplantation in patients with newly diagnosed multiple myeloma: results of an IFM phase II study. *Haematologica* 91, 1498-1505 (2006).
27. Sasgary, M., Ahmad, R. U., Schwarz, H. P., Turecek, P. L. & Reipert, B. M. Single cell analysis of factor VIII-specific T cells in hemophilic mice after treatment with human factor VIII. *Thromb Haemost* 87, 266-272 (2002).
28. Wu, H., et al. Mechanism of the immune response to human factor VIII in murine hemophilia A. *Thromb Haemost* 85, 125-133 (2001).
29. Davidoff, A. M., Ng, C. Y., Zhou, J., Spence, Y. & Nathwani, A. G. Sex significantly influences transduction of murine liver by recombinant adeno-associated viral vectors through an androgen-dependent pathway. *Blood* 102, 480-488 (2003).
30. Yan, Z., et al. Ubiquitination of both adeno-associated virus type 2 and 5 capsid proteins affects the transduction efficiency of recombinant vectors. *J Virol* 76, 2043-2053 (2002).
31. Zhong, L., et al. Tyrosine-phosphorylation of AAV2 vectors and its consequences on viral intracellular trafficking and transgene expression. *Virology* (2008).
32. Zhong, L., et al. Next generation of adeno-associated virus 2 vectors: point mutations in tyrosines lead to high-efficiency transduction at lower doses. *Proc Natl Aced Sci USA* 105, 7827-7832 (2008).
33. Finn, J. D., et al. Proteasome Inhibitors Decrease AAV2 Capsid derived Peptide Epitope Presentation on MHC Class I Following Transduction. *Mol Ther* (2009).
34. Muchamuel, T., et al. A selective inhibitor of the immunoproteasome subunit LMP7 blocks cytokine production and attenuates progression of experimental arthritis. *Nat Med* 15, 781-787 (2009).
35. Blanco, B., at al. Bortezomib induces selective depletion of alloreactive T lymphocytes and decreases the production of Th1 cytokines. *Blood* 107, 3575-3583 (2006).
36. Elliott, P. J., Zollner, T. M. & Boehncke, W. H. Proteasome inhibition: a new anti-inflammatory strategy. *J Mol Med* 81, 235-245 (2003).
37. Everly, J. J., Walsh, R. C., Alloway, R. R. & Woodle, E. S. Proteasome inhibition for antibody-mediated rejection. *Curr Opin Organ Transplant* (2009).
38. Khan, S., et al. Immunoproteasomes largely replace constitutive proteasomes during an antiviral and antibacterial immune response in the liver. *J Immunol* 167, 6859-6868 (2001).
39. Choi, V. W., Asokan, A., Haberman, R. A. & Samulski, R. J. Production of recombinant adeno-associated viral vectors for in vitro and in vivo use. *Curr Protoc Mol Biol* Chapter 16, Unit 16 25 (2007).
40. Cockrell, A. S., Ma, H., Fu, K., McCown, T. J. & Kafri, T. A trans-lentiviral packaging cell line for high-titer conditional self-inactivating HIV-1 vectors. *Mol Ther* 14, 276-284 (2006).
41. Mount, J. D., at al. Sustained phenotypic correction of hemophilia B dogs with a factor IX null mutation by liver-directed gene therapy. *Blood* 99, 2670-2676 (2002).
42. Waters, B., et al. Anti-CD3 prevents factor VIII inhibitor development in hemophilia A mice by a regulatory CD4+CD25+-dependent mechanism and by shifting cytokine production to favor a Th1 response. *Blood* 113, 193-203 (2009).
43. Zhang, T. P., et al. Transgene expression levels and kinetics determine risk of humoral immune response modeled in factor IX knockout and missense mutant mice. *Gene Ther* 14, 429-440 (2007).
44. Herzog, R. W., Mount, J. D., Arruda, V. R., High, K. A. & Lothrop, C. D., Jr. Muscle-directed gene transfer and transient immune suppression result in sustained partial correction of canine hemophilia B caused by a null mutation. *Mol Ther* 4, 192-200 (2001).
45. Thomas, C. E., Storm, T A, Huang, Z. & Kay, M. A. Rapid uncoating of vector genomes is the key to efficient liver transduction with pseudotyped adeno-associated virus vectors. *J Virol* 78, 3110-3122 (2004).

TABLE 1

Proteasome inhibitor increases nuclear accumulation of genomes in vivo

| Treatment | Cytoplasm | Nucleus | Ratio N/C |
|---|---|---|---|
| AAV8-cFVIII | 4.46 ± 0.7 | 5.52 ± 0.96 | 1.23 ± 0.96 |
| AAV8-cFVIII + Bortezomib | 1.2 ± 0.91 | 9.08 ± 2.61 | 7.57 ± 3.62* |

Abbreviations: cFVIII, canine factor VIII; N/C, Nuclear/cytoplasm
Data are represented as mean ± SEM
*$P < 0.05$

TABLE 2

Effect of dexamethasone co-administration to decrease transgene expression outside of the liver:
AAV8.Luciferase -mediated luminescence and vector genome persistence

| | Whole Animal | | Liver | | Heart | | Pancreas | | Spleen | | Testis | |
|---|---|---|---|---|---|---|---|---|---|---|---|---|
| | Tissue Luminescence | VG/cell | Tissue Luminescence | VG/cell | Tissue Luminescence | VG/cell | Tissue Luminescence | VG/cell | Tissue Luminescence | VG/cell | Tissue Luminescence | VG/cell |
| Vector only (No dex) | $1.2 \pm 1.4 \times 10^8$ | N/A | $5.6 \pm 1.3 \times 10^6$ | 1 | $81.5 \pm 57.0 \times 10^3$ | 0.13 | $56.2 \pm 65.1 \times 10^2$ | 1.3 | $17.6 \pm 2.2 \times 10^2$ | 0.1 | $2.3 \pm 2.7 \times 10^3$ | <0.01 |
| Vector + Dex 0.2 mg | $1.7 \pm 1.2 \times 10^8$ | N/A | $12.0 \pm 0.3 \times 10^6$ | 2.5 | $4.5 \pm 1.7 \times 10^3$ | 0.09 | $1.6 \pm 0.9 \times 10^2$ | 0.05 | $1.6 \pm 0.9 \times 10^2$ | 0.05 | $0.4 \pm 0.2 \times 10^3$ | <0.01 |

*All other organs sites <1 × 10e4 counts/mg protein and <0.1 vg/cell, including brain, lung, stomach, ileum, skeletal muscle.
Dexamethasone 0.2 mg is approximately equal to 8.0 mg/kg as a single dose.

TABLE 3

Anti-cFVIII inhibitor development after AAV2 and AAV8 treatment in FVIII$^{-/-}$ mice

| | Animals with Inhibitor/Total animals | Time of onset after vector (week) | Inhibitor titer (range) |
|---|---|---|---|
| AAV2-cFVIII | 1/5 | 8 | 0.4-0.5 BIU |
| AAV2-cFVIII + Bortezomib | 2/6 | 4 and 8 | 0.4-1.2 BIU |
| AAV8-cFVIII | 6/10 | 8-20 | 1.2-10.4 BIU |
| AAV8-cFVIII + Bortezomib | 5/15 | 2-20 | 1.0-13.2 BIU |
| AAV8-cFVIII + Bortezomib + Dex | 2/10 | 6 and 20 | 0.5-2.4 BIU |

Abbreviations: cFVIII, canine factor VIII; Dex, Dexamethasone; BIU, Bethesda Units; wk, week.

TABLE 4

Summary of hemophilia A dogs undergoing AAV-mediated gene therapy with proteasome inhibitor

| | | | | Whole Blood Clotting Time Assays | | Bleeding frequency | | Inhibitor | |
|---|---|---|---|---|---|---|---|---|---|
| | | | | # Values Corrected | | | | | |
| Dog | Sex | Treatment | # Assays | to Normal Range (% of total assays) | At year 1 (#) | Total (#/time) | | status (BIU) | Outcome |
| Cindy | F | AAV8 | 26 | 1 (4%) | 9 | 12/18 months | | 0 | Fatal hemorrhage |
| Mike | M | AAV8 | 26 | 4 (15.4%) | 9 | 16/25 months | | 0 | Fatal hemorrhage |
| Boober | M | AAV8 | 18 | 0 (0%) | NA | 11/10 ms | | 0 | Alive |
| Carl | M | AAV8 + Bortezomib | 34 | 20 (58.8%) | 0 | 1/32.5 ms | | 0 | Alive |
| Greg | M | AAV8 + Bortezomib + Dexamethasone | 34 | 20 (58.8%) | 0 | 2/32.5 ms | | 0 | Alive |
| Sprocket | F | AAV8 + Bortezomib | 20 | 4 (20%) | NA | 2/11 ms | | 0 | Alive |
| Marjorie | F | AAV8 + Bortezomib + Dexamethasone | 20 | 8 (40%) | NA | 0/11 ms | | 0 | Alive |
| Denver | M | No treatment | | | | 10/22 ms | | NA | Alive |
| Bass | M | No treatment | | | | 13/22 ms | | NA | Alive |
| Gator | M | No treatment | | | | 10/22 ms | | NA | Alive |

*Age at vector administration = 1 month. Dose of vector = 1 × 10$^{13}$ vg/kg; WBCT, whole blood clotting time; Normal value of 6-10 minutes for WBCT; WBCT expressed as numbers in normal range in the total measurements; ms, months; NA, not applicable

TABLE 5

| | GenBank Accession No. |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |

TABLE 5-continued

| | GenBank Accession No. |
|---|---|
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

What is claimed is:

1. A composition comprising:
    (a) an adeno-associated virus (AAV) vector comprising an AAV vector genome comprising a heterologous nucleic acid encoding a protein selected from the group consisting of Factor VIII (FVIII), dystrophin, mini-dystrophin and cystic fibrosis transmembrane regulator protein (CFTR), wherein the AAV vector genome is oversized relative to a wild type AAV genome; and
    (b) bortezomib.

2. The composition of claim 1, wherein the size of the AAV vector genome is greater than about 5.0 kb.

3. The composition of claim 1, wherein the AAV vector genome is a double-stranded AAV vector genome.

4. The composition of claim 1, wherein the AAV vector is a split transgene AAV vector.

5. The composition of claim 1, wherein the heterologous nucleic acid comprises a coding sequence that has been optimized for enhanced expression.

6. The composition of claim 1, wherein the heterologous nucleic acid comprises noncoding sequences that have been optimized for enhanced expression.

7. The composition of claim 1, wherein the AAV vector genome has been optimized for enhanced expression.

8. A pharmaceutical formulation comprising a composition according to claim 1 in a pharmaceutically acceptable carrier.

9. A method of delivering the heterologous nucleic acid to a cell, comprising contacting the cell with the composition of claim 1.

10. The method of claim 9, wherein the cell is a muscle cell, a liver cell, a cell in a joint or a cell in a osteochondral site.

11. A method of delivering the heterologous nucleic acid to a subject, comprising administering to the subject the composition of claim 1.

12. The method of claim 11, wherein the subject is a human.

13. A method of delivering a heterologous nucleic acid to a subject, comprising administering to the subject an AAV vector comprising an AAV vector genome comprising a heterologous nucleic acid encoding a protein selected from the group consisting of FVIII, dystrophin, mini-dystrophin and CFTR, wherein the AAV vector genome is oversized relative to a wild type AAV genome; and bortezomib, wherein the AAV vector is administered to the subject before, and/or after administration of the bortezomib with or without concurrent administration of the bortezomib.

* * * * *